(12) United States Patent
Case et al.

(10) Patent No.: US 8,872,912 B2
(45) Date of Patent: Oct. 28, 2014

(54) HIGH SPEED DISTRIBUTED OPTICAL SENSOR INSPECTION SYSTEM

(75) Inventors: Steven K. Case, St. Louis Park, MN (US); Beverly Caruso, legal representative, St. Louis Park, MN (US); Todd D. Liberty, Apple Valley, MN (US); Timothy A. Skunes, Mahtomedi, MN (US); Carl E. Haugan, St. Paul, MN (US); Chuanqi Chen, Singapore (SG)

(73) Assignee: CyberOptics Corporation, Golden Valley, MN (US)

( * ) Notice: Subject to any disclaimer, the term of this patent is extended or adjusted under 35 U.S.C. 154(b) by 964 days.

(21) Appl. No.: 12/940,214

(22) Filed: Nov. 5, 2010

(65) Prior Publication Data

US 2011/0102575 A1    May 5, 2011

Related U.S. Application Data

(63) Continuation-in-part of application No. 12/886,803, filed on Sep. 21, 2010, and a continuation-in-part of (Continued)

(51) Int. Cl.
| | |
|---|---|
| *H04N 9/47* | (2006.01) |
| *G06K 9/00* | (2006.01) |
| *G01N 21/88* | (2006.01) |
| *H05K 13/08* | (2006.01) |
| *G06K 9/20* | (2006.01) |
| *G01N 21/956* | (2006.01) |

(52) U.S. Cl.
CPC ............ *H05K 13/08* (2013.01); *G01N 21/8806* (2013.01); *G06K 9/2036* (2013.01); *G01N 21/956* (2013.01)
USPC .............................................. 348/92; 348/147

(58) Field of Classification Search
USPC ................ 382/147, 149, 152; 348/43, 92, 87; 414/222.01; 101/126
See application file for complete search history.

(56) References Cited

U.S. PATENT DOCUMENTS

| 1,577,388 A | 5/1923 | Twyman |
| 4,677,473 A | 6/1987 | Okamoto |

(Continued)

FOREIGN PATENT DOCUMENTS

| DE | 202008004430 | 1/2009 |
| EP | 0301255 | 2/1989 |

(Continued)

OTHER PUBLICATIONS

Martin, "A practical Guide to Machine Vision Lighting", Advance Illumination, Rochester, VT, United States, Oct. 2007.

(Continued)

*Primary Examiner* — Gims Philippe
(74) *Attorney, Agent, or Firm* — Christopher R. Christenson; Kelly, Holt & Christenson, PLLC

(57) ABSTRACT

An electronics assembly line includes a first electronics assembly machine and a second electronics assembly machine. The first electronics assembly machine has a first electronics assembly machine outlet. The second electronics assembly machine has a second electronics assembly machine inlet and outlet. The inlet of the second electronics assembly machine is coupled to the outlet of the first electronics assembly machine by a conveyor. A first optical inspection sensor is disposed over the conveyor before the inlet of the second electronics assembly and is configured to provide first sensor inspection image data relative to a substrate that passes beneath the first optical inspection sensor in a non-stop fashion. A second optical inspection sensor is disposed over the conveyor after the outlet of the second electronics assembly machine and is configured to provide second sensor inspection image data relative to a substrate that passes beneath the second optical inspection sensor in a non-stop fashion. A computer is operably coupled to the first and second optical inspection sensors and is configured to provide an inspection result based upon at least one of the first and second inspection image data.

24 Claims, 28 Drawing Sheets

Related U.S. Application Data application No. 12/864,110, filed on Jan. 21, 2011, and a continuation-in-part of application No. 12/564,131, filed on Sep. 22, 2009.

(60) Provisional application No. 61/244,616, filed on Sep. 22, 2009, provisional application No. 61/244,671, filed on Sep. 22, 2009.

(56) References Cited

U.S. PATENT DOCUMENTS

| | | | |
|---|---|---|---|
| 4,750,798 A | 6/1988 | Whitehead | |
| 4,795,913 A | 1/1989 | Blessing et al. | 250/559.36 |
| 4,799,175 A | 1/1989 | Sano | |
| 4,896,211 A | 1/1990 | Hung | |
| 4,978,224 A | 12/1990 | Kishimoto et al. | |
| 4,993,826 A | 2/1991 | Yoder | |
| 5,039,868 A | 8/1991 | Kobayashi | |
| 5,058,178 A | 10/1991 | Ray | |
| 5,058,982 A | 10/1991 | Katzir | |
| 5,060,065 A | 10/1991 | Wasserman | |
| 5,086,397 A | 2/1992 | Schuster | |
| 5,153,668 A | 10/1992 | Katzir | |
| 5,245,421 A | 9/1993 | Robertson | |
| 5,260,779 A | 11/1993 | Wasserman | |
| 5,291,239 A | 3/1994 | Jackson | |
| 5,347,363 A | 9/1994 | Yamanaka | |
| 5,455,870 A | 10/1995 | Sepai | |
| 5,517,234 A | 5/1996 | Straayer et al. | |
| 5,550,583 A | 8/1996 | Amir | |
| 5,684,530 A | 11/1997 | White | |
| 5,696,591 A | 12/1997 | Bilhorn | |
| 5,822,055 A | 10/1998 | Tsai | |
| 5,825,495 A | 10/1998 | Huber | |
| 5,880,772 A | 3/1999 | Kalnajs | |
| 6,020,957 A | 2/2000 | Rosengaus et al. | 356/237.4 |
| 6,023,663 A | 2/2000 | Kim | |
| 6,175,107 B1 | 1/2001 | Juvinall | |
| 6,222,624 B1 | 4/2001 | Yonezawa | |
| 6,362,877 B1 | 3/2002 | Kobayashi | |
| 6,577,405 B2 | 6/2003 | Kranz et al. | |
| 6,603,103 B1 | 8/2003 | Ulrich et al. | 250/205 |
| 6,633,375 B1 | 10/2003 | Veith | |
| 6,750,899 B1 | 6/2004 | Fishbaine et al. | 348/126 |
| 6,757,966 B2 | 7/2004 | Inoue | |
| 6,850,855 B2 | 2/2005 | Kawai | |
| 7,019,826 B2 | 3/2006 | Vook | |
| 7,027,639 B2 | 4/2006 | Fishbaine | 382/150 |
| 7,075,565 B1 | 7/2006 | Raymond | |
| 7,310,438 B2 | 12/2007 | Prince | |
| 7,372,632 B2 | 5/2008 | Lizotte | 359/626 |
| 7,394,084 B2 | 7/2008 | Kuriyama et al. | 250/559.34 |
| 7,460,219 B2 | 12/2008 | Jung | |
| 7,590,279 B2 * | 9/2009 | Akiyama | 382/147 |
| 7,828,472 B2 | 11/2010 | Liu et al. | |
| 8,098,372 B2 | 1/2012 | Eitan et al. | 356/237.2 |
| 2002/0089664 A1 | 7/2002 | Shibata | |
| 2003/0039388 A1 | 2/2003 | Ulrich et al. | |
| 2003/0110610 A1 | 6/2003 | Duquette et al. | |
| 2003/0179369 A1 | 9/2003 | Feldman | |
| 2003/0227618 A1 | 12/2003 | Some | |
| 2004/0037677 A1 * | 2/2004 | Koyama et al. | 414/222.01 |
| 2004/0156539 A1 | 8/2004 | Jansson | |
| 2005/0219518 A1 | 10/2005 | Korngut | |
| 2005/0259245 A1 | 11/2005 | Cemic | |
| 2006/0062013 A1 | 3/2006 | Imade | |
| 2007/0160283 A1 * | 7/2007 | Saphier et al. | 382/152 |
| 2008/0156207 A1 * | 7/2008 | Ellenbogen | 101/126 |
| 2009/0148033 A1 * | 6/2009 | Alumot et al. | 382/149 |
| 2011/0069154 A1 | 3/2011 | Case | |
| 2011/0069507 A1 | 3/2011 | Haugan | |
| 2011/0069878 A1 | 3/2011 | Case | |
| 2011/0075156 A1 | 3/2011 | Patel et al. | 356/603 |
| 2011/0090333 A1 | 4/2011 | Haugan | |
| 2011/0175997 A1 | 7/2011 | Case | |
| 2012/0133920 A1 | 5/2012 | Skunes et al. | 356/23 |
| 2012/0327215 A1 | 12/2012 | Case et al. | |

FOREIGN PATENT DOCUMENTS

| | | |
|---|---|---|
| EP | 0994646 | 4/2000 |
| EP | 1578186 | 9/2005 |
| EP | 1694109 A2 | 8/2006 |
| GB | 2271683 | 4/1994 |
| GB | 2417072 | 2/2006 |
| GB | 2444409 | 6/2008 |
| JP | 61134718 | 6/1986 |
| JP | 6229875 | 12/1987 |
| JP | 63011842 | 1/1988 |
| JP | 02268260 | 11/1990 |
| JP | 08327561 | 12/1996 |
| JP | 2002271099 A | 9/2002 |
| JP | 2006324599 | 11/2006 |
| WO | WO 98/19200 A1 | 5/1998 |
| WO | WO 00/26640 | 5/2000 |
| WO | WO 00/38494 | 6/2000 |
| WO | WO 0196839 A1 | 12/2001 |
| WO | WO 2009/014940 | 1/2009 |

OTHER PUBLICATIONS

Scharstein and Szeliski, "A Taxonomy and Evaluation of Dense Two-Frame Stereo Correspondence Algorithms"Microsoft Research, Microsoft Corporation, Redmond, WA.

Smith, "Modern Optical Engineering: The Design of Optical Systems", 4th ed. New York: McGraw-Hill, 2008.

Kang, Web, Zitinick, and Takeo, "A Multibaseline Stereo System with Active Illumination and Real-time Image Acquisition."

Collins, "A Space-Sweep Approach to True Multi-Image Matching" University of Massachusetts, Amherst, MA.

CyberOptics, "Flex Ultra TM HR, Automated Optical Inspection", CyberOptics Corporation 2007.

Notification of transmittal of the International Search Report and the Written Opinion for International application No. PCT/US2009/031744 dated May 18, 2009.

Notification of transmittal of the International Search Report and the Written Opinion for International application No. PCT/US2010/049619 dated Dec. 8, 2010.

Notification of transmittal of the International Search Report and the Written Opinion for International application No. PCT/US2010/049617 dated Dec. 8, 2010.

Notification of transmittal of the International Search Report and the Written Opinion for International application No. PCT/US2010/055452 dated Jan. 17, 2011.

U.S. Appl. No. 12/864,110, filed Jul. 22, 2010.
U.S. Appl. No. 12/564,131, filed Sep. 22, 2009.
U.S. Appl. No. 12/886,784, filed Sep. 21, 2010.
U.S. Appl. No. 12/886,803, filed Sep. 21, 2010.
U.S. Appl. No. 12/939,267, filed Nov. 4, 2010.

Written Opinion for International application No. PCT/US2010/049617 dated Feb. 14, 2012.

Notification of Transmittal of International Preliminary Report on Patentability for the International application No. PCT/US10/49617 dated Aug. 24, 2012.

Notification of transmittal of the International Search Report and the Written Opinion for International application No. PCT/US2011/059040 dated Jul. 20, 2012.

Invitation to Pay Additional Fees from International patent application No. PCT/US2011/059040 dated Mar. 15, 2012.

Related U.S. Appl. No. 13/480,079, filed May 24, 2012.

* cited by examiner

HIGH SPEED DISTRIBUTED OPTICAL SENSOR INSPECTION SYSTEM

CROSS-REFERENCE TO RELATED APPLICATION

The present application is a Continuation-In-Part application of U.S. patent application Ser. No. 12/886,803, filed Sep. 21, 2010, which application is based on and claims the benefit of U.S. Provisional Application Ser. No. 61/244,616, filed Sep. 22, 2009 and U.S. Provisional Application Ser. No. 61/244,671, filed on Sep. 22, 2009; and is a Continuation-In-Part application of U.S. patent application Ser. No. 12/864,110 filed Jul. 22, 2010; and is a Continuation-In-Part application of U.S. patent application Ser. No. 12/564,131, filed Sep. 22, 2009. All applications listed above are herein incorporated by reference in their entireties.

COPYRIGHT RESERVATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Automated electronics assembly machines are often used in the manufacture of printed circuit boards, which are used in various electronic devices. The manufacturing process is generally required to operate quite swiftly. Rapid or high speed manufacturing ensures that costs of the completed printed circuit board are minimized. However, the speed with which printed circuit boards are manufactured must be balanced by the acceptable level of scrap or defects caused by the process. Printed circuit boards can be extremely complicated and small and any one board may have a vast number of components and consequently a vast number of electrical connections. Printed circuit boards are now produced in large quantities. Since such printed circuit boards can be quite expensive and/or be used in expensive equipment, it is important that they be produced accurately and with high quality, high reliability, and minimum scrap. Unfortunately, because of the manufacturing methods available, some level of scrap and rejects still occurs. Typical faults on printed circuit boards include inaccuracy of placement of components on the board, which might mean that the components are not correctly electrically connected in the board. Another typical fault occurs when an incorrect component is placed at a given location on a circuit board. Additionally, the component might simply be absent, or it may be placed with incorrect electrical polarity. Further still, if there are insufficient solder paste deposits, this can lead to poor connections. Additionally, if there is too much solder paste, such a condition can lead to short circuits, and so on. Further still, other errors may prohibit, or otherwise inhibit, electrical connections between one or more components, and the board. An example of this condition is when a small, "stray" electrical component is accidentally released onto a section of the circuit board where another component is to be subsequently placed by another placement operation. This stray component may prevent electrical connectivity of the "correct" component that is placed onto the printed circuit board after the stray component. The condition if further exacerbated when the correct component has a package style, such as a ball grid array (BGA) or flip chip, where the electrical connections are visibly hidden after placement. In this condition, the stray component and the integrity of the solder joints cannot be visibly inspected either manually or by automated optical inspection (AOI) systems for errors or defects since the defects are hidden by the component package. X-ray systems may detect these errors, but these systems remain too slow and expensive for wide spread adoption in most printed circuit board assembly lines.

Conventional automated optical inspection systems receive a substrate, such as a printed circuit board, either immediately after placement of the components upon the printed circuit board and before wave soldering, or post reflow. Typically, the systems include a conveyor that is adapted to move the substrate under test through an optical field of view that acquires one or more images and analyzes those images to automatically derive conclusions about components on the substrate and/or the substrate itself. The amount of time to initially program the inspection inputs is often high for these systems and also to fine tune the inspection parameters or models. Another drawback to these automated optical inspection systems is that, although they can identify manufacturing errors, they often provide little help to identify the particular processes that caused the manufacturing error. As such, a need has arisen to provide an improved inspection system that simplifies the initial inspection programming as well as providing additional insight into the root cause of manufacturing errors.

SUMMARY

An electronics assembly line includes a first electronics assembly machine and a second electronics assembly machine. The first electronics assembly machine has a first electronics assembly machine outlet. The second electronics assembly machine has a second electronics assembly machine inlet and outlet. The inlet of the second electronics assembly machine is coupled to the outlet of the first electronics assembly machine by a conveyor. A first optical inspection sensor is disposed over the conveyor before the inlet of the second electronics assembly and is configured to provide first sensor inspection image data relative to a substrate that passes beneath the first optical inspection sensor in a non-stop fashion. A second optical inspection sensor is disposed over the conveyor after the outlet of the second electronics assembly machine and is configured to provide second sensor inspection image data relative to a substrate that passes beneath the second optical inspection sensor in a non-stop fashion. A computer is operably coupled to the first and second optical inspection sensors and is configured to provide an inspection result based upon at least one of the first and second inspection image data.

DETAILED DESCRIPTION OF ILLUSTRATIVE EMBODIMENTS

Figure 1:
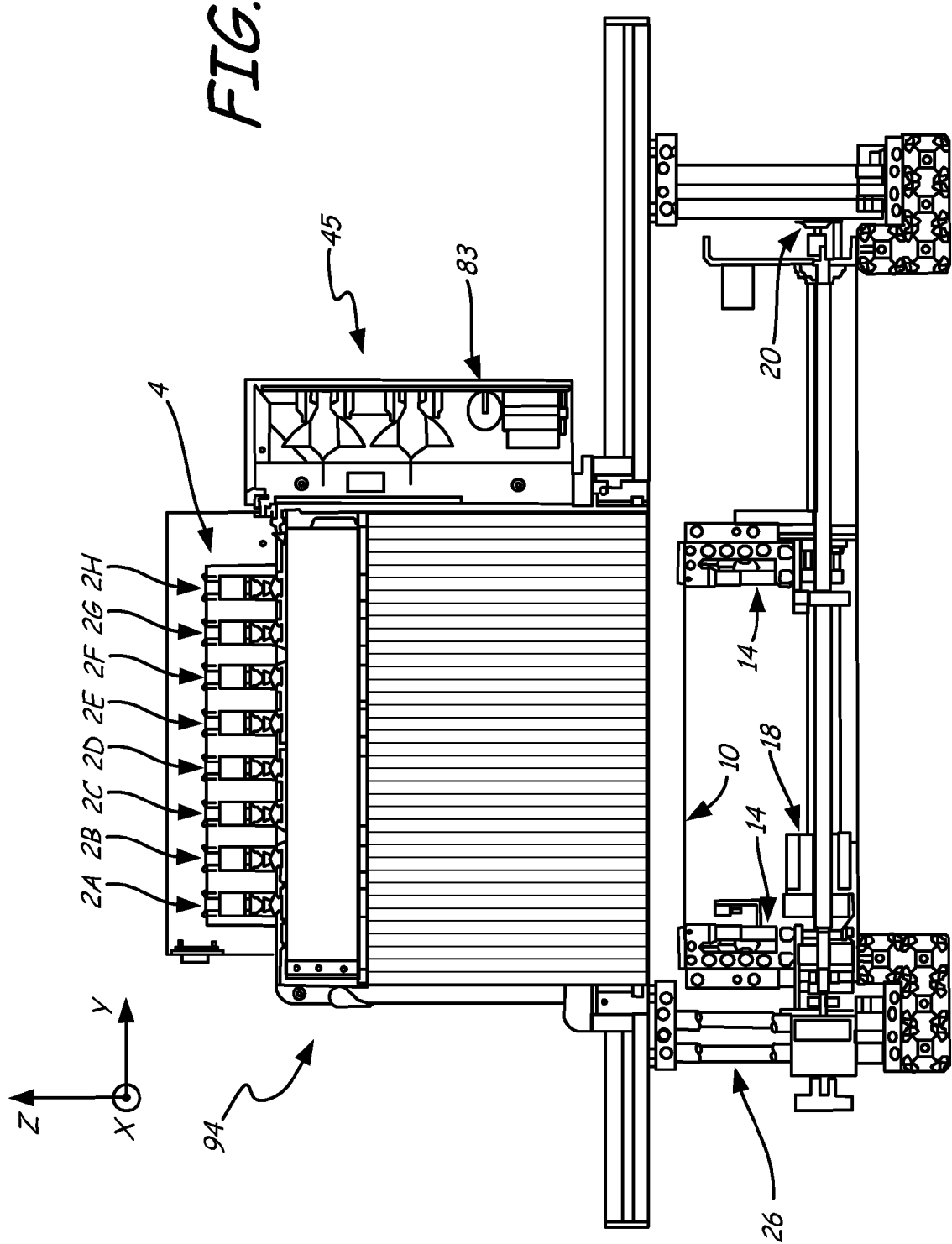
FIG. 1 is a cross-sectional elevation view of an automated high speed optical inspection system with a camera array and compact, integrated illuminator in accordance with embodiment of the present invention.

Embodiments of the present invention will generally be described with respect to the figures. A number of reference numerals are used to refer to the various features of the figures. For clarity, a listing of the various reference numerals follows.

Reference Numbers:
2—camera
3—camera array
4—camera array
5—camera array
10—printed circuit board
11—small workpiece
13—component
14—belt
15—component
18—motor
20—encoder
22—programmable logic controller
24—panel sensor
26—workpiece transport conveyor
30—camera field of view
32—camera array field of view
33—camera array field of view
34—camera array field of view
35—camera array field of view
36—camera array field of view
40—illuminator
41—illuminator
42—illuminator
43—illuminator
44—illuminator
45—illuminator
46—LED
48—linear light source
50—aperture
52—diffuser plate
53—diffuser plate
54—mirror
56—aperture
57—mixing chamber
58—top aperture plate
59—top aperture plate
60—light source
62—collimated light ray bundle
64—light pipe
65—light pipe illuminator
66—light pipe side wall
67—mirrors
68—light pipe exit aperture
69—light pipe entrance aperture
70—reflective surface 71—inspection application program
72—conveyor interface
73—inspection application program
76—system computer
77—system computer
80—main electronics board
82—image memory
83—strobe assembly
84—strobe board
86—strobe monitor
87—flash lamp
88—flash lamp
92—inspection system
94—optical inspection sensor
98—optical inspection sensor
100—solder paste deposit
101—solder paste deposit
110—circuit board assembly line
112—screen printer
114—pick and place
116—pick and place
118—reflow oven
120—automated optical inspection system
122—conveyor
124—conveyor
126—conveyor
128—conveyor
130—optical inspection sensor
132—optical inspection sensor
134—optical inspection sensor
136—example image
138—example image
140—difference image Embodiments of the present invention generally provide an inspection system and method with high speed acquisition of multiple illumination images without the need for expensive and sophisticated motion control hardware. Processing of the images acquired with different illumination types may appreciably enhance the inspection results.

FIG. 1 shows a cross-sectional elevation view of a system for generating high contrast, high speed digital images of a workpiece that are suitable for automated inspection, in accordance with an embodiment of the present invention. Camera array 4 consists of cameras 2A through 2H preferably arranged at regular intervals. Each camera 2A through 2H simultaneously images and digitizes a rectangular area on a workpiece or substrate, such as printed circuit board 10, while the workpiece undergoes relative movement with respect to cameras 2A through 2H. Illuminator 45 provides a series of pulsed, short duration illumination fields referred to as strobed illumination. The short duration of each illumination field effectively "freezes" the image of printed circuit board 10 to suppress motion blurring. Two or more sets of images for each location on printed circuit board 10 are generated by camera array 4 with different illumination field types for each exposure. Depending on the particular features on printed circuit 10 board that need to be inspected, the inspection results may be appreciably enhanced by joint processing of the reflectance images generated with different illumination field types. Further details of illuminator 45 are provided in the discussion of FIGS. 21 and 22.

Workpiece transport conveyor 26 translates printed circuit board 10 in the X direction in a nonstop mode to provide high speed imaging of printed circuit board 10 by camera array 4. Conveyor 26 includes belts 14 which are driven by motor 18. Optional encoder 20 measures the position of the shaft of motor 18 hence the approximate distance traveled by printed circuit board 10 can be calculated. Other methods of measuring and encoding the distance traveled of printed circuit board 10 include time-based, acoustic or vision-based encoding methods. By using strobed illumination and not bringing printed circuit board 10 to a stop, the time-consuming transport steps of accelerating, decelerating, and settling prior to imaging by camera array 4 are eliminated. It is believed that the time required to entirely image a printed circuit board 10 of dimensions 210 mm×310 mm can be reduced from 11 seconds to 4 seconds using embodiments of the present invention compared to coming to a complete stop before imaging.

Figure 2:
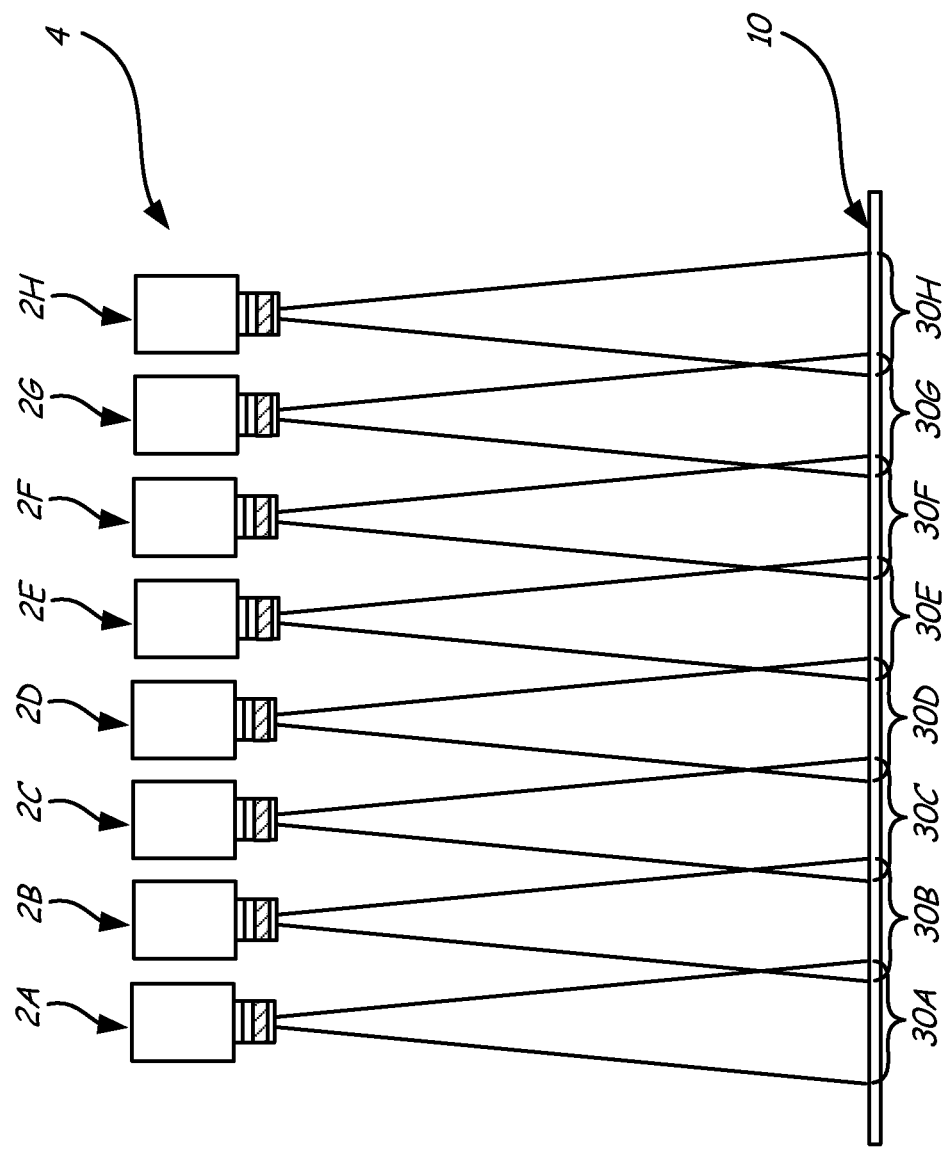
FIG. 2 is a diagrammatic elevation view of a plurality of cameras having overlapping fields of view in accordance with an embodiment of the present invention.

FIG. 2 shows the Y dimension location of each field of view 30A through 30H on printed circuit board 10 that is imaged by cameras 2A through 2H, respectively. There is a slight overlap between adjacent fields of view in order to completely image all locations on printed circuit board 10. During the inspection process, the images of discrete fields of view 30A through 30H are digitally merged, or stitched, into one continuous image in the overlap regions. Example camera array 4 is shown in FIGS. 1 and 2 arranged as a single dimensional array of discrete cameras. As shown, cameras 2A-2H are configured to image in a non-telecentric manner. This has the advantage that the fields of view 30A through 30H can be overlapped. However, the magnification, or effective resolution, of a non-telecentric imaging system will change as printed circuit 10 and its features are positioned closer or further away from cameras 2A-2H. Effects of circuit board 10 warpage, thickness variations and other camera alignment errors can be compensated by image stitching. In another embodiment, the camera array may be arranged in a two dimensional array. For example, the discrete cameras may be arranged into a camera array of two columns of four cameras where adjacent fields of view overlap. Other arrangements of the camera array may be advantageous depending on cost, speed, and performance goals of the inspection system, including arrays where the fields of view do not overlap. For example, a staggered array of cameras with telecentric imaging systems may be used.

Figure 3:
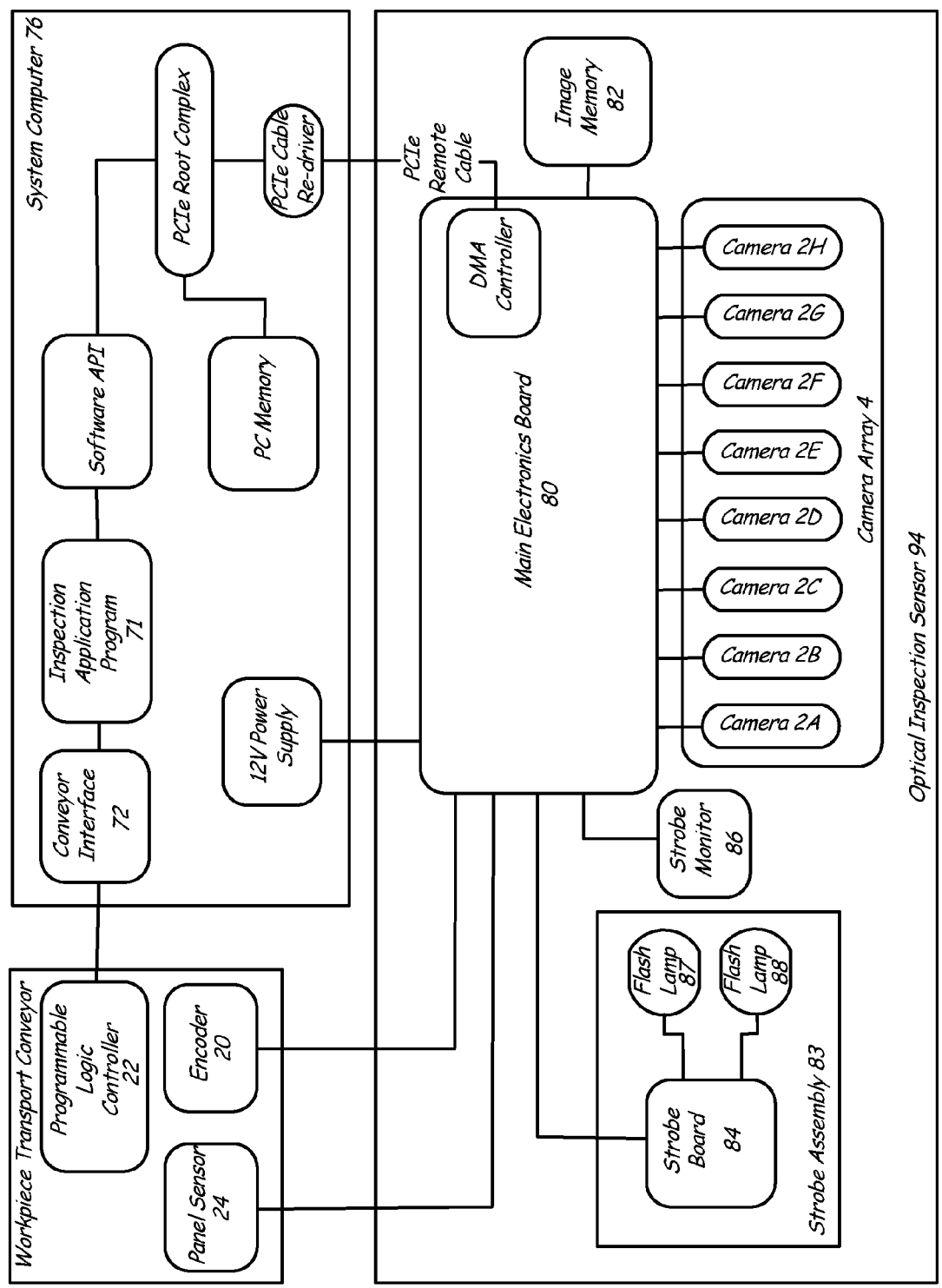
FIG. 3 is a system block diagram of an inspection system in accordance with an embodiment of the present invention.

FIG. 3 is a block diagram of inspection system 92. Inspection application program 71 preferably executes on system computer 76. Inputs into inspection program 71 include the type of printed circuit board 10, CAD information describing the location and types of components on printed circuit board 10, the features on printed circuit board 10 to be inspected, lighting and camera calibration data, the transport conveyor 26 direction, et cetera. Inspection program 71 configures programmable logic controller 22 via conveyor interface 72 with the transport direction, velocity, and width of printed circuit board 10. Inspection program 71 also configures main electronics board 80 via PCI express interface with the number of encoder 20 counts between each subsequent image acquisition of camera array 4. Alternatively, a time-based image acquisition sequence may be executed based on the known velocity of printed circuit board 10. Inspection program 71 also programs or otherwise sets appropriate configuration parameters into cameras 2A-2H prior to an inspection as well as strobe board 84 with the individual flash lamp output levels.

Panel sensor 24 senses the edge of printed circuit board 10 as it is loaded into inspection system 92 and this signal is sent to main board 80 to begin an image acquisition sequence. Main board 80 generates the appropriate signals to begin each image exposure by camera array 4 and commands strobe board 84 to energize the appropriate flash lamps 87 and 88 at the proper time. Strobe monitor 86 senses a portion of light emitted by flash lamps 87 and 88 and this data may be used by main electronics board 80 to compensate image data for slight flash lamp output variations. Image memory 82 is provided and preferably contains enough capacity to store all images generated for at least one printed circuit board 10. For example, in one embodiment, each camera in the array of cameras has a resolution of about 5 megapixels and memory 82 has a capacity of about 2.0 gigabytes. Image data from cameras 2A-2H may be transferred at high speed into image memory buffer 82 to allow each camera to be quickly prepared for subsequent exposures. This allows the printed circuit board 10 to be transported through inspection system 92 in a nonstop manner and generate images of each location on printed circuit board 10 with at least two different illumination field types. The image data may begin to be read out of image memory 82 into PC memory over a high speed electrical interface such as PCI Express (PCIe) as soon as the first images are transferred to memory 82. Similarly, inspection program 71 may begin to compute inspection results as soon as image data is available in PC memory.

The image acquisition process will now be described in further detail with respect to FIGS. 4-6.

Figure 4:
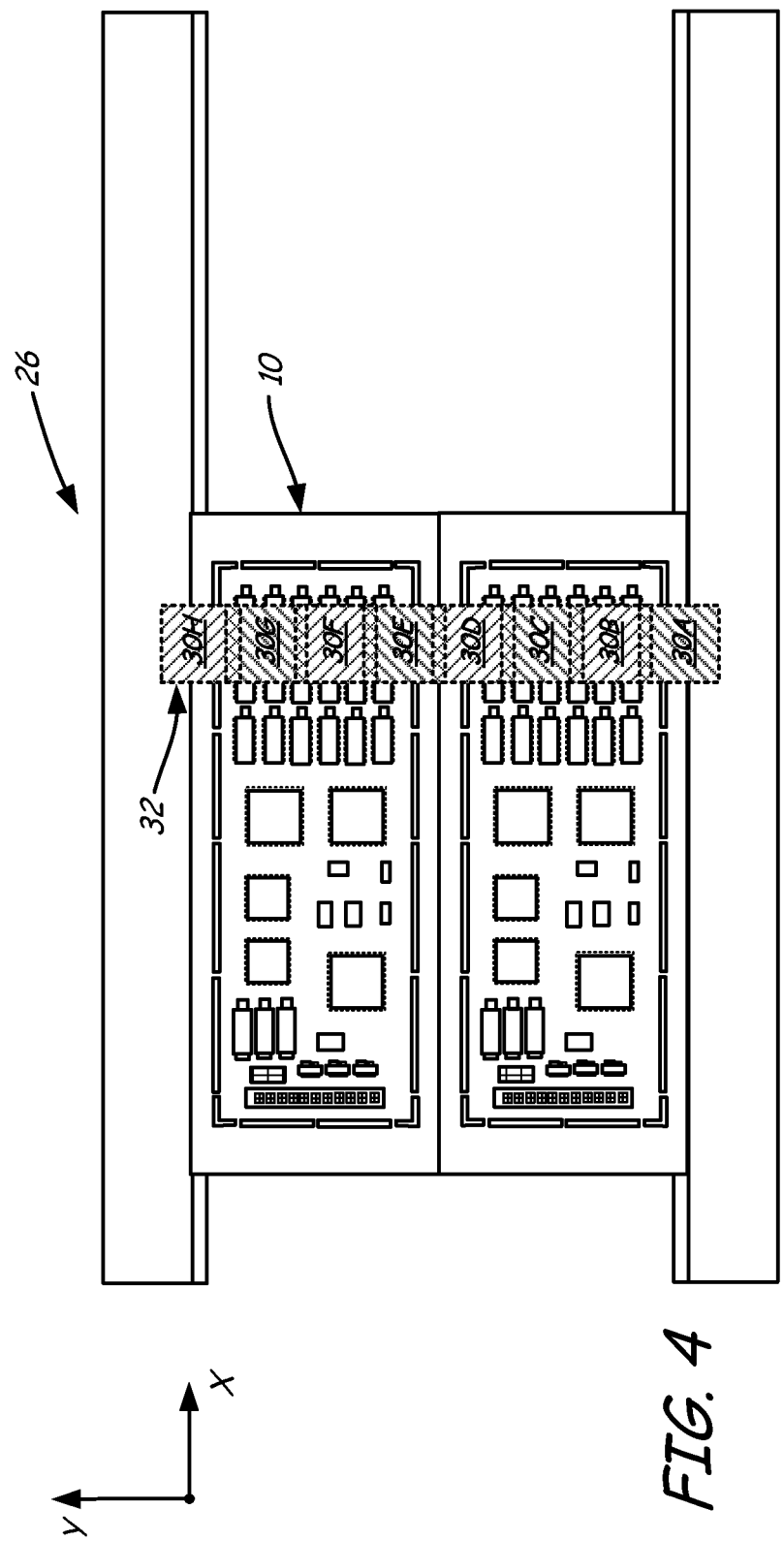
FIG. 4 is a top plan view of a transport conveyor, printed circuit board, and a camera array field of view acquired with a first illumination field type.

FIG. 4 shows a top plan view of transport conveyor 26 and printed circuit board 10. Cameras 2A-2H image overlapping fields of view 30A-30H, respectively, to generate effective field of view 32 of camera array 4. Field of view 32 is acquired with a first strobed illumination field type. Printed circuit board 10 is transported by conveyor 26 in a nonstop manner in the X direction. Printed circuit board 10 preferably travels at a velocity that varies less than five percent during the image acquisition process, although larger velocity variations and accelerations may be accommodated.

In one preferred embodiment, each field of view 30A-30H has approximately 5 million pixels with a pixel resolution of 17 microns and an extent of 33 mm in the X direction and 44 mm in the Y direction. Each field of view 30A-30H overlaps neighboring fields of view by approximately 4 mm in the Y direction so that center-to-center spacing for each camera 2A-2H is 40 mm in the Y direction. In this embodiment, camera array field of view 32 has a large aspect ratio in the Y direction compared to the X direction of approximately 10:1.

Figure 5:
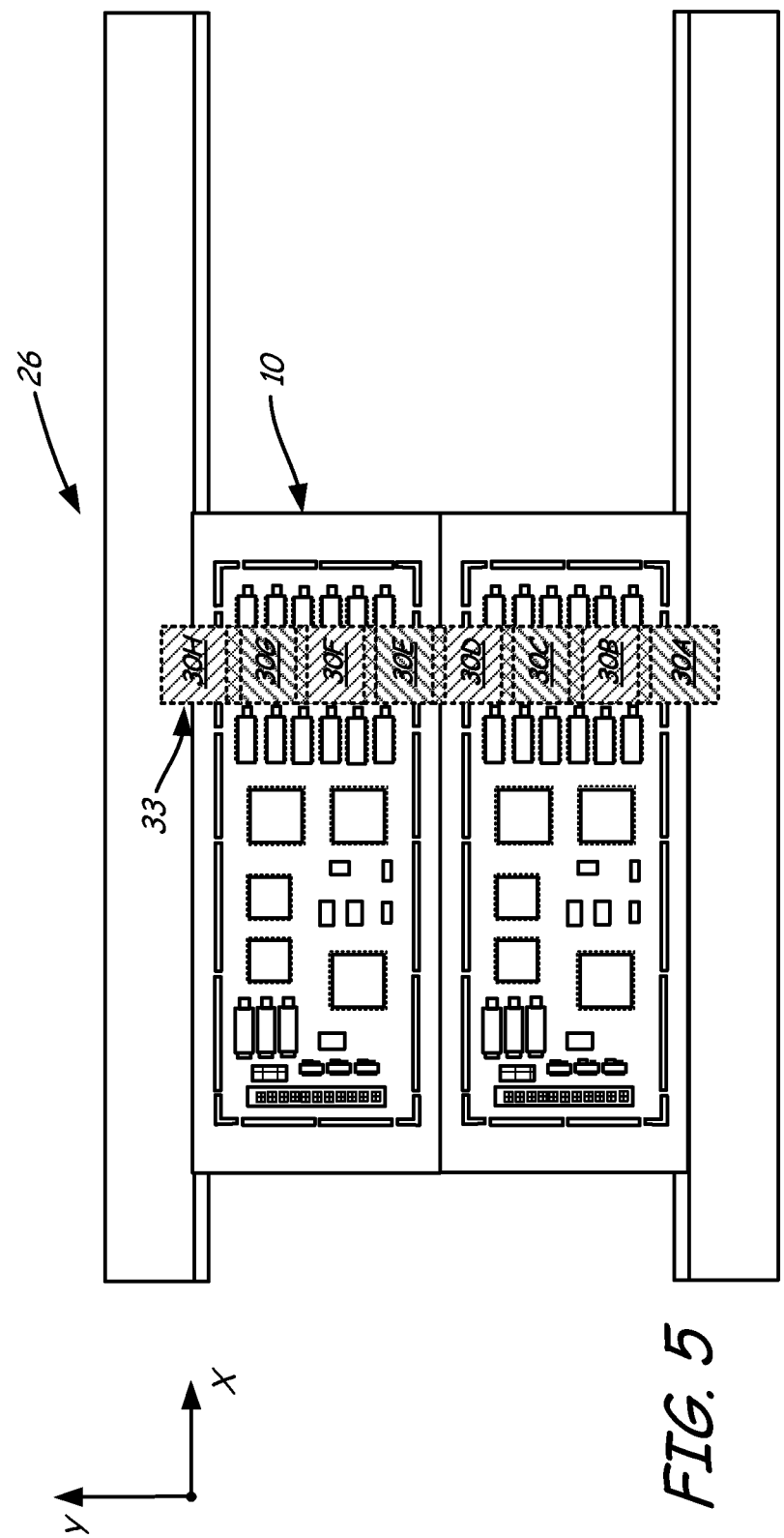
FIG. 5 is a top plan view of a transport conveyor, printed circuit board, and a camera array field of view acquired with a second illumination field type.

FIG. 5 shows printed circuit board 10 at a location displaced in the positive X direction from its location in FIG. 4. For example, printed circuit board 10 may be advanced approximately 14 mm from its location in FIG. 4. Effective field of view 33 is composed of overlapping fields of view 30A-30H and is acquired with a second illumination field type.

Figure 6A:
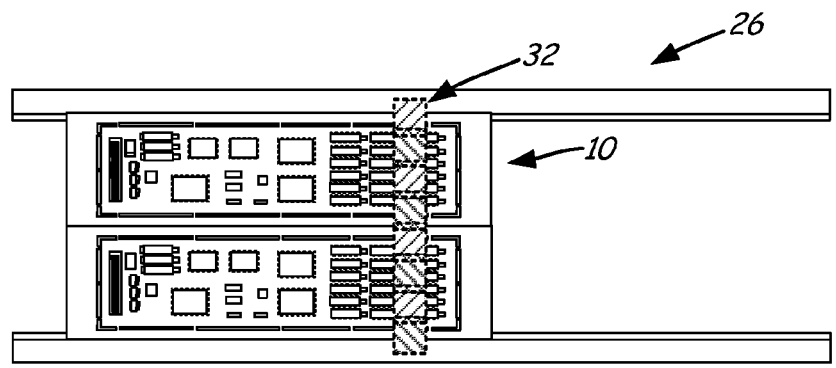
FIGS. 6A-6D illustrate a workpiece and camera array fields of view acquired at different positions and under alternating first and second illumination field types in accordance with an embodiment of the present invention.
Figure 6B:
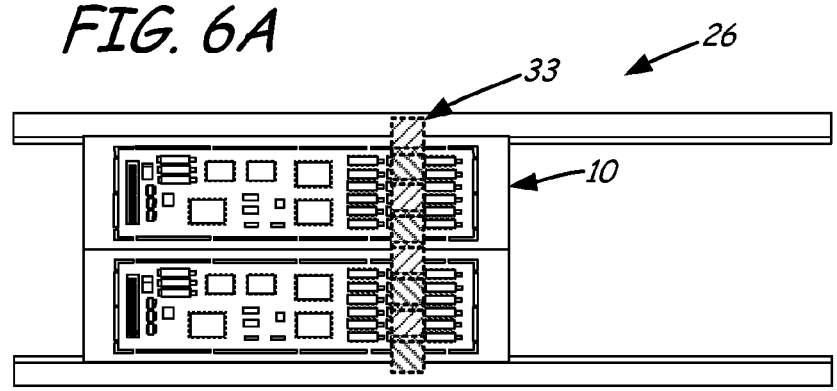
Figure 6C:
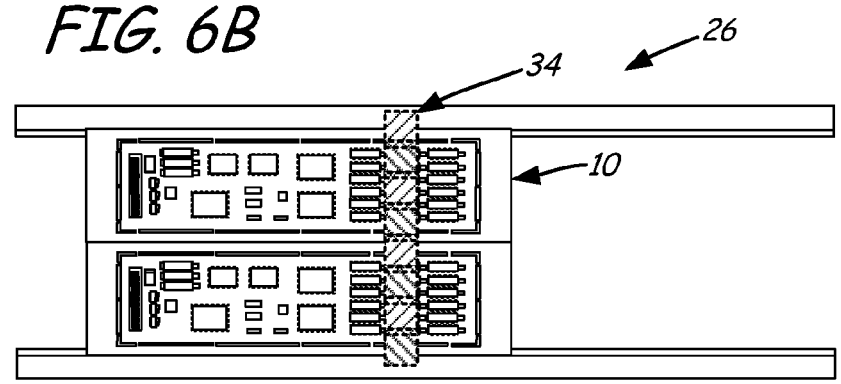
Figure 6D:
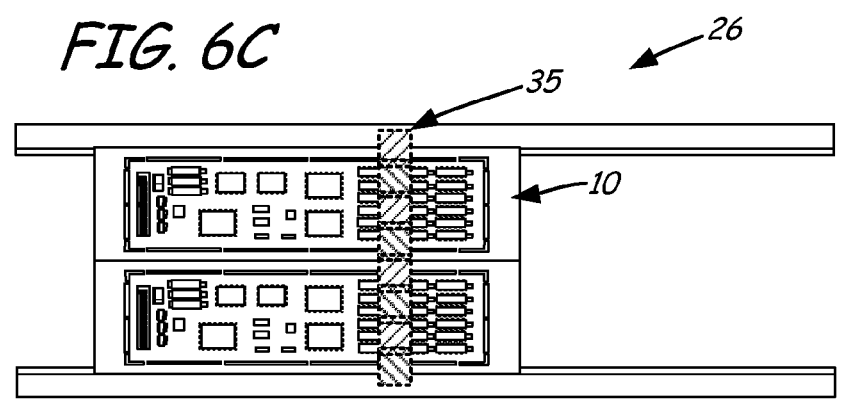

FIGS. 6A-6D show a time sequence of camera array fields of view 32-35 acquired with alternating first and second illumination field types. It is understood that printed circuit board 10 is traveling in the X direction in a nonstop fashion. FIG. 6A shows printed circuit board 10 at one X location during image acquisition for the entire printed circuit board 10. Field of view 32 is acquired with a first strobed illumination field type as discussed with respect to FIG. 4. FIG. 6B shows printed circuit board 10 displaced further in the X direction and field of view 33 acquired with a second strobed illumination field type as discussed with respect to FIG. 5. FIG. 6C shows printed circuit board 10 displaced further in the X direction and field of view 34 acquired with the first illumination field type and FIG. 6D shows printed circuit board 10 displaced further in the X direction and field of view 35 acquired with the second illumination field type.

There is a small overlap in the X dimension between field of views 32 and 34 in order to have enough overlapping image information in order to register and digitally merge, or stitch together, the images that were acquired with the first illumination field type. There is also small overlap in the X dimension between field of views 33 and 35 in order to have enough overlapping image information in order to register and digitally merge the images that were acquired with the second illumination field type. In the embodiment with fields of view 30A-30H having extents of 33 mm in the X direction, it has been found that an approximate 5 mm overlap in the X direction between field of views acquired with the same illumination field type is effective. Further, an approximate 14 mm displacement in the X direction between fields of view acquired with different illumination types is preferred.

Images of each feature on printed circuit board 10 may be acquired with more than two illumination field types by increasing the number of fields of view collected and ensuring sufficient image overlap in order to register and digitally merge, or stitch together, images generated with like illumination field types. Finally, the stitched images generated for each illumination type may be registered with respect to each other. In a preferred embodiment, workpiece transport conveyor 26 has lower positional accuracy than the inspection requirements in order to reduce system cost. For example, encoder 20 may have a resolution of 100 microns and conveyor 26 may have positional accuracy of 0.5 mm or more. Image stitching of fields of view in the X direction compensates for positional errors of the circuit board 10.

It is desirable that each illumination field is spatially uniform and illuminates from consistent angles. It is also desirable for the illumination system to be compact and have high efficiency. Limitations of two prior art illumination systems, linear light sources and ring lights, will be discussed with reference to FIGS. 7-9. Linear light sources have high efficiency, but poor uniformity in the azimuth angle of the projected light. Ring light sources have good uniformity in the azimuth angle of the projected light, but are not compact and have poor efficiency when used with large aspect ratio camera arrays.

Figure 7:
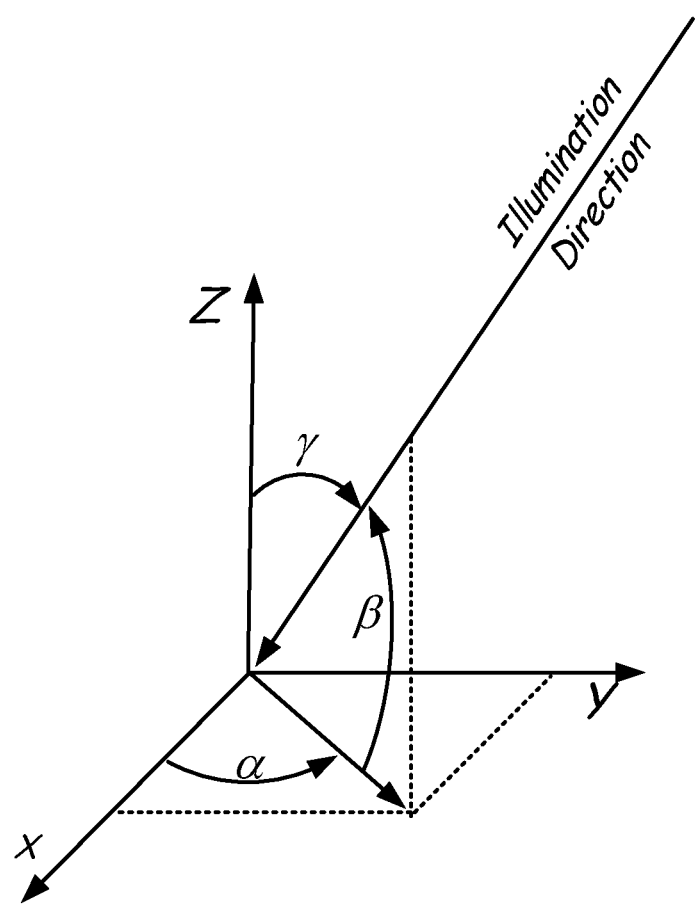
FIG. 7 is a coordinate system for defining illumination direction.

FIG. 7 defines a coordinate system for illumination. Direction Z is normal to printed circuit board 10 and directions X and Y define horizontal positions on printed circuit board 10 or other workpiece. Angle $\beta$ defines the elevation angle of the illumination. Angle $\gamma$ redundantly defines the illumination ray angle with respect to normal. Angle $\alpha$ is the azimuth angle of the ray. Illumination from nearly all azimuth and elevation angles is termed cloudy day illumination. Illumination predominantly from low elevation angles, $\beta$, near horizontal is termed dark field illumination. Illumination predominantly from high elevation angles, $\beta$, near vertical is termed bright field illumination. A good, general purpose, illumination system will create a light field with uniform irradiance across the entire field of view (spatial uniformity) and will illuminate from consistent angles across the entire field of view (angle uniformity).

Figure 8:
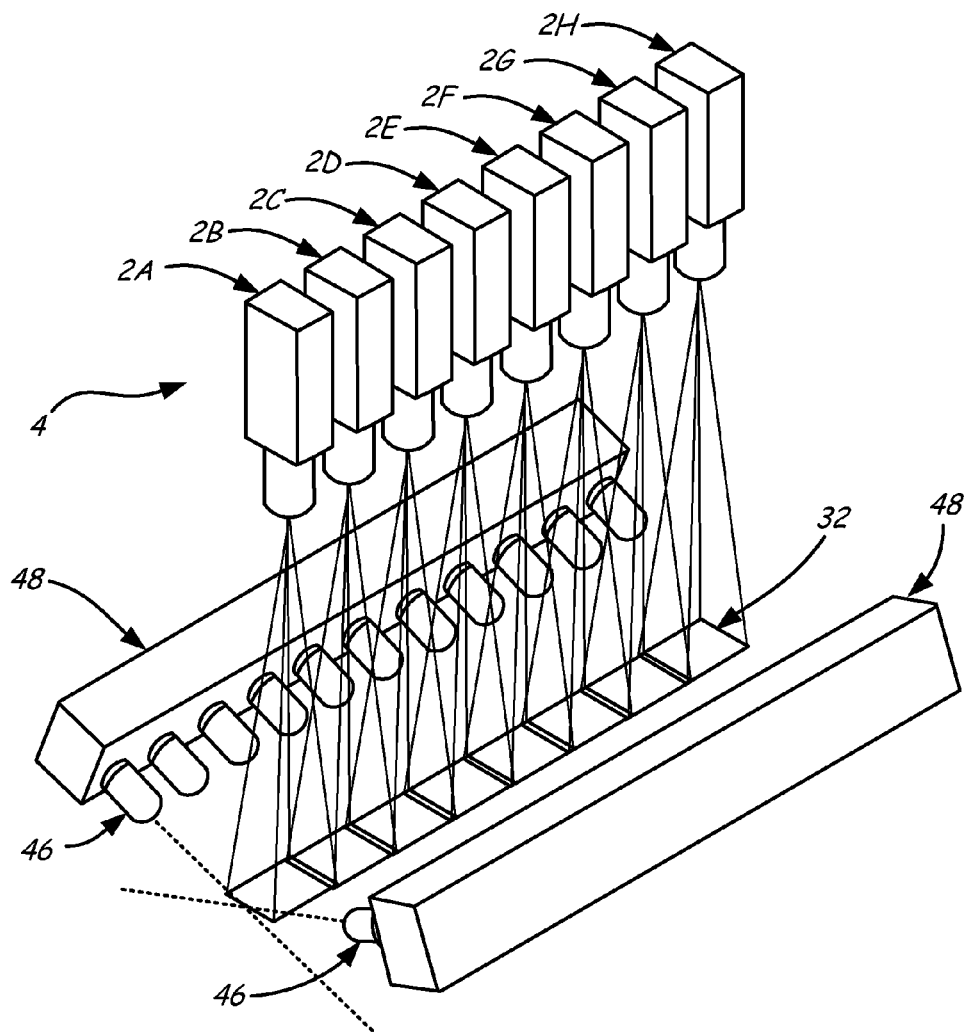
FIG. 8 is a perspective view of a known linear line source illuminating a camera array field of view.

FIG. 8 shows known linear light sources 48 illuminating camera array field of view 32. Linear light source 48 can use an array of LEDs 46 to efficiently concentrate light on a narrow rectangular field of view 32. A disadvantage of using linear light sources 48 is that although the target receives symmetrical illumination from the two directions facing the sources, no light is received from the directions facing the long axis of the FOV.

Figure 9:
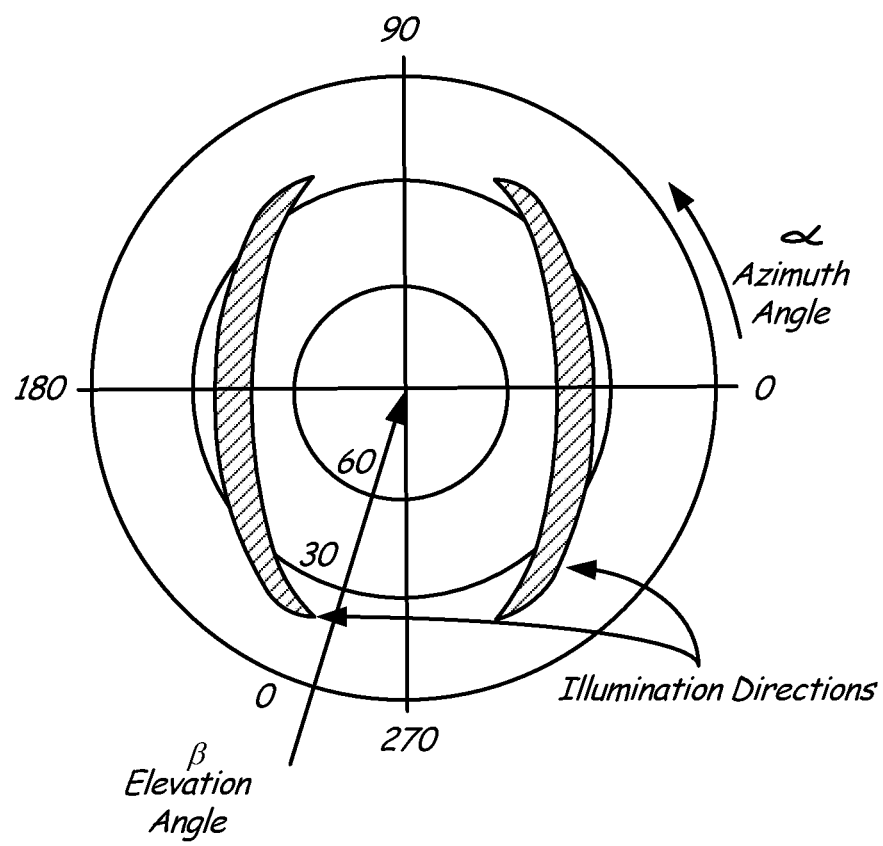
FIG. 9 is a polar plot of the illumination directions of the illuminator shown in FIG. 8.

FIG. 9 is a two axis polar plot showing illumination directions for the two linear light sources 48. The polar plot shows that strong illumination is received by camera array field of view 32 from the direction nearest to light sources 48 (at 0 and 180 degree azimuth angles) and that no illumination received from the 90 and 270 degrees azimuth angle. As the azimuth angle varies between 0 and 90 the source elevation angle drops and the source subtends a smaller angle so less light is received. Camera array field of view 32 receives light which varies in both intensity and elevation angle with azimuth angle. The linear light sources 48 efficiently illuminate field of view 32, but with poor uniformity in azimuth angle. In contrast, known ring lights have good uniformity in azimuth, but must be made large in order to provide acceptable spatial uniformity for large aspect ratio camera field of 32.

Although a ring light could be used to provide acceptable uniformity in azimuth, the ring light would need to be very large to provide acceptable spatial uniformity for camera field of view 32 of approximately 300 mm in the Y direction. For typical inspection applications, it is believed that the ring light would need to be over 1 meter in diameter to provide sufficient spatial uniformity. This enormous ring fails to meet market needs in several respects: the large size consumes valuable space on the assembly line, the large light source is expensive to build, the illumination angles are not consistent across the working field, and it is very inefficient—the light output will be scattered over a significant fraction of the 1 meter circle while only a slim rectangle of the board is actually imaged.

An optical device, referred to as a light pipe, can be used to produce a very uniform light field for illumination. For example, U.S. Pat. No. 1,577,388 describes a light pipe used to back illuminate a film gate. Conventional light pipes, however, need to be physically long to provide uniform illumination.

Figure 10:
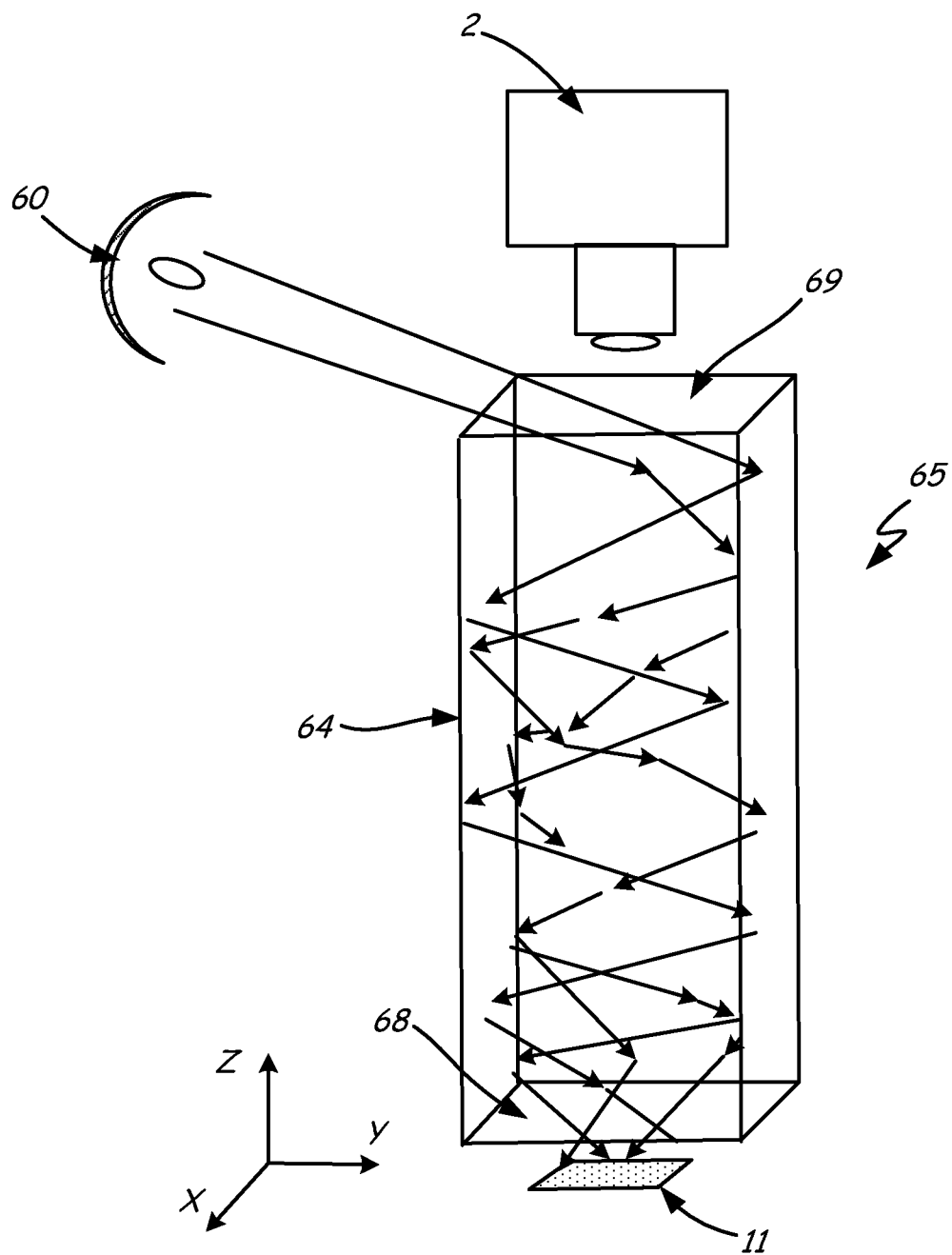
FIG. 10 is a perspective view of an example hollow light pipe illuminator in accordance with an embodiment of the present invention.
Figure 11:
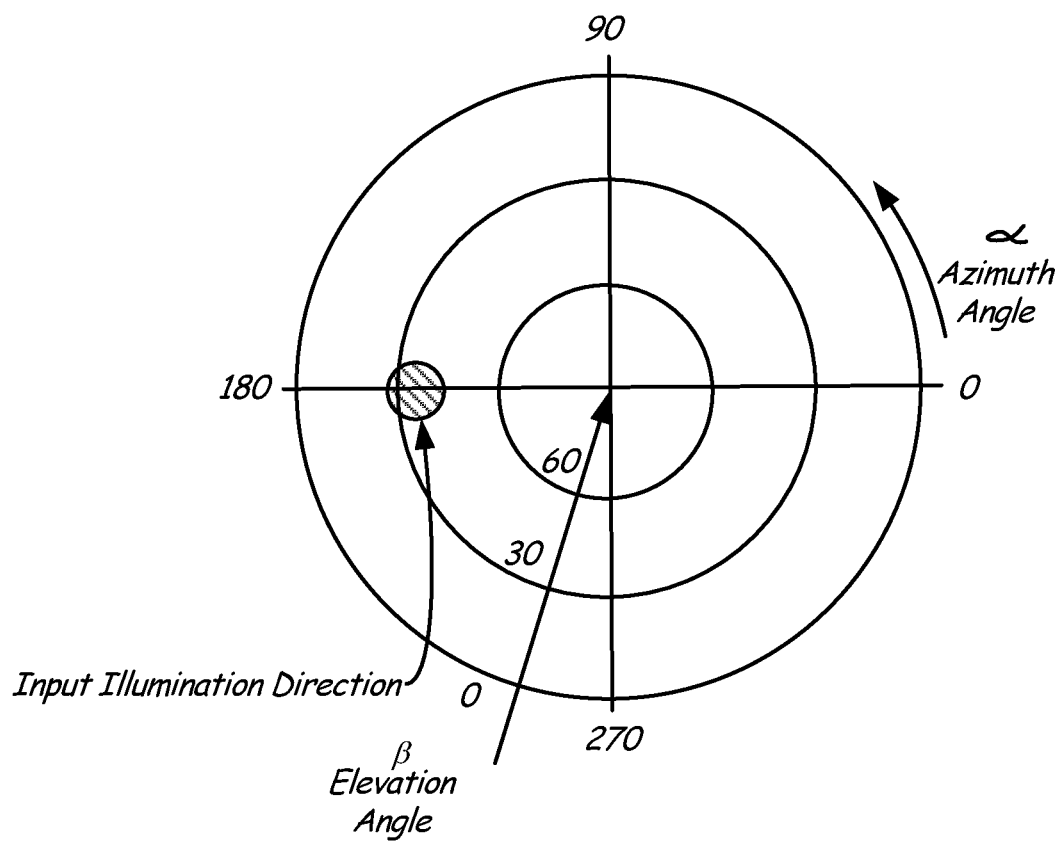
FIG. 11 is a polar plot of the input illumination direction of the illuminator shown in FIG. 10.
Figure 12:
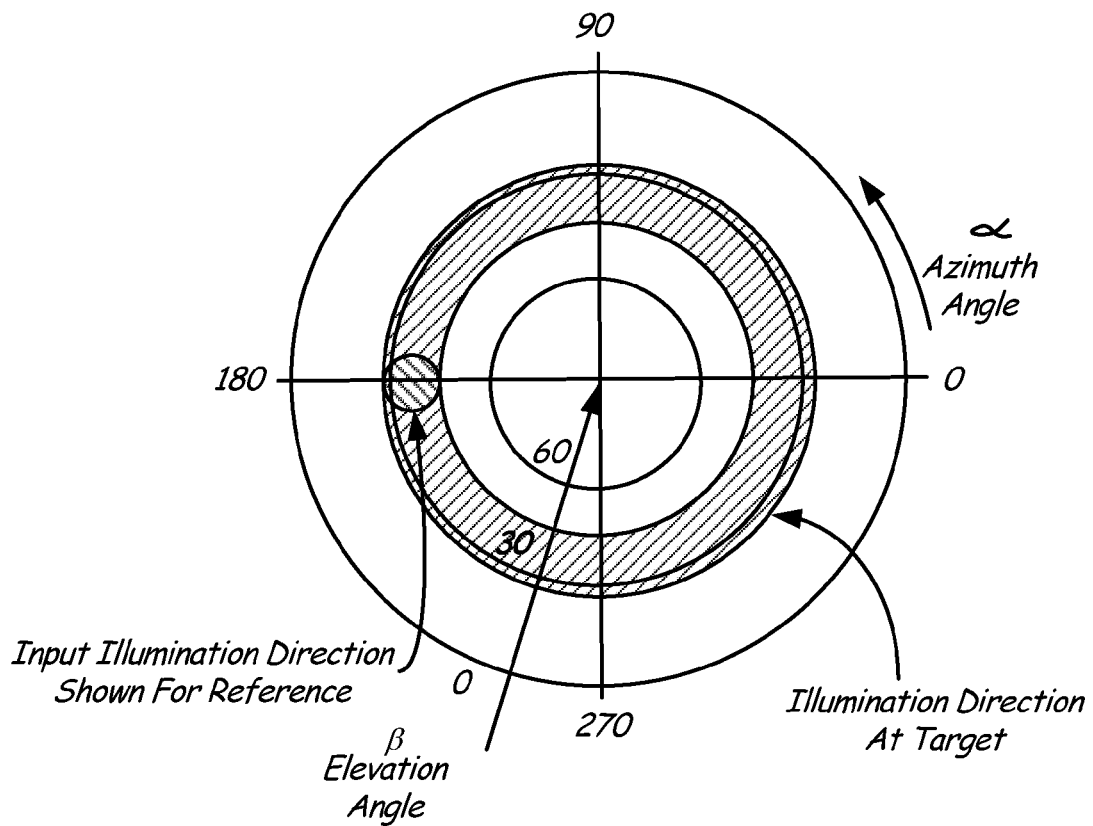
FIG. 12 is a polar plot of the output illumination directions of the illuminator shown in FIG. 10.

A brief description of light pipe principles is provided with respect to FIGS. 10-12. Embodiments of the present invention are then described with respect to FIGS. 13-17 that significantly reduce the length of a light pipe required for uniform illumination. In one embodiment, the interior walls of the light pipe are constructed with reflective materials that scatter light in only one direction. In another embodiment of the present invention, the light pipes are configured with input and output ports that allow simple integration of a camera array to acquire images of a uniformly and efficiently illuminated workpiece.

FIG. 10 shows illuminator 65 which consists of light source 60 and light pipe 64. Hollow box light pipe 64 which, when used as described, will generate a uniform dark field illumination pattern. Camera 2 views workpiece 11 down the length of light pipe 64 through apertures 67 and 69 at the ends of the light pipe. A light source 60, for example an arc in a parabolic reflector, is arranged such that it projects light into the entrance aperture 67 of light pipe 64 with internally reflecting surfaces such that light descends at the desired elevation angle. Alternatively a lensed LED or other source may be used as long as the range of source elevation angles matches the desired range of elevation angles at workpiece 11. The light source may be either strobed or continuous. The fan of rays from light source 60 proceeds across the pipe and downward until it strikes one of the side walls. The ray fan is split and spread in azimuth at the corners of the pipe but the elevation angle is preserved. This expanded ray fan then spreads out, striking many different side wall sections where it is further spread and randomized in azimuth angle and largely unchanged in elevation angle. After a number of reflections all azimuth angles are present at exit aperture 68 and workpiece 11. Therefore all points on the target are illuminated by light from all azimuth angles but only those elevation angles present in the original source. In addition, the illumination field at workpiece 11 is spatially uniform. Note that the lateral extent of light pipe 64 is only slightly larger than the field of view in contrast to the required size of a ring light for the condition of spatially uniform illumination.

FIG. 11 shows the polar plot of the illumination direction at the source, a nearly collimated bundle of rays from a small range of elevation and azimuth angles.

FIG. 12 is a polar plot of the rays at workpiece 11 and the angular spread of the source is included for comparison. All azimuth angles are present at workpiece 11 and the elevation angles of the source are preserved.

As the elevation angle of light exiting illuminator 65 is the same as those present in the source 60, it is relatively easy to tune those angles to specific applications. If a lower elevation illumination angle is desired then the source may be aimed closer to the horizon. The lower limit to the illumination angle is set by the standoff of the light pipe bottom edge as light cannot reach the target from angles below the bottom edge of the light pipe. The upper limit to the illumination elevation angle is set by the length of light pipe 66 since several reflections are required to randomize, or homogenize, the illumination azimuth angle. As elevation angle is increased there will be fewer bounces for a given length light pipe 64 before reaching workpiece 11.

The polygonal light pipe homogenizer only forms new azimuth angles at its corners, therefore many reflections are needed to get a uniform output If all portions of the light pipe side walls could spread or randomize the light pattern in the azimuth direction, then fewer reflections would be required and the length of the light pipe in the Z direction could be reduced making the illuminator shorter and/or wider in the Y direction.

Figure 13:
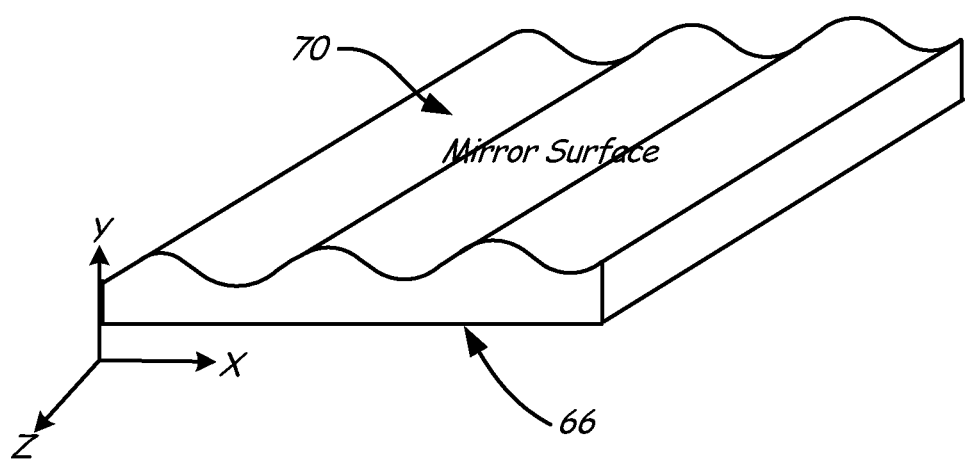
FIG. 13 is a perspective view of a reflective surface of a light pipe wall in accordance with an embodiment of the present invention.
Figure 14A:
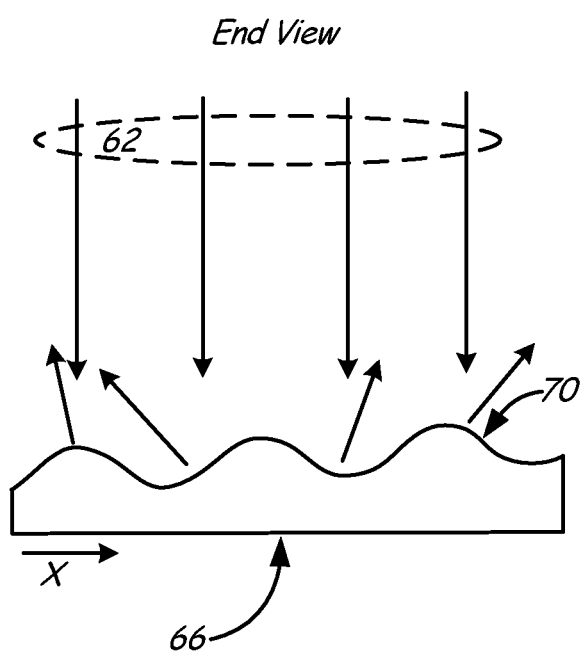
FIGS. 14A-B are cross sectional views of the reflective surface shown in FIG. 13
Figure 14B:
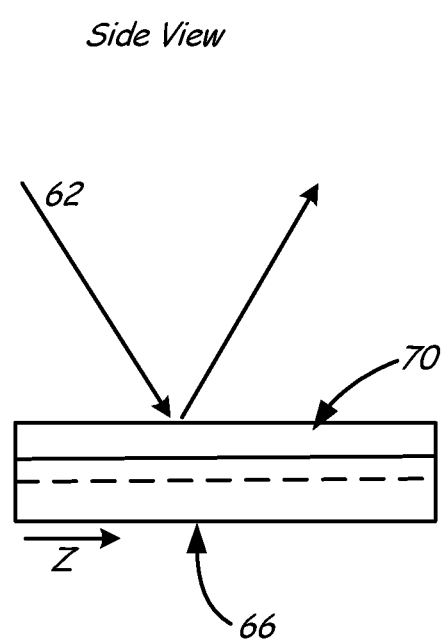

FIGS. 13 and 14 illustrate an embodiment of the present invention with light pipe side walls which diffuse or scatter light in only one axis. In this embodiment it is preferred that the azimuth angles of the light bundle be spread on each reflection while maintaining elevation angles. This is achieved by adding curved or faceted, reflective surface 70 to the interior surface of light pipe side wall 66 as shown in FIG. 13. Cross sectional views of side wall 66 are shown in FIGS. 14A and 14B. FIG. 14A demonstrates how a collimated light ray bundle 62 is spread perpendicular to the axis of the cylindrical curvature on reflective surface 70. In FIG. 14B, the angle of reflection for light ray bundle 62 is maintained along the axis of the cylindrical curvature on reflective surface 70. Hence, the elevation angle of the source is maintained since the surface normal at every point of reflector 70 has no Z component. The curved, or faceted, surface of reflective surface 70 creates a range of new azimuth angles on every reflection over the entire surface of the light pipe wall 66 and therefore the azimuth angle of the source is rapidly randomized. Embodiment of the present invention can be practiced using any combination of refractive, diffractive and reflective surfaces for the interior surface of light pipe side wall 66.

In one aspect, reflective surface 70 is curved in segments of a cylinder. This spreads incoming light evenly in one axis, approximating a one-dimensional Lambertian surface, but does not spread light in the other axis. This shape is also easy to form in sheet metal. In another aspect, reflective surface 70 has a sine wave shape. However, since a sine wave shape has more curvature at the peaks and valleys and less curvature on the sides, the angular spread of light bundle 62 is stronger at the peaks and valleys than on the sides.

Figure 15A:
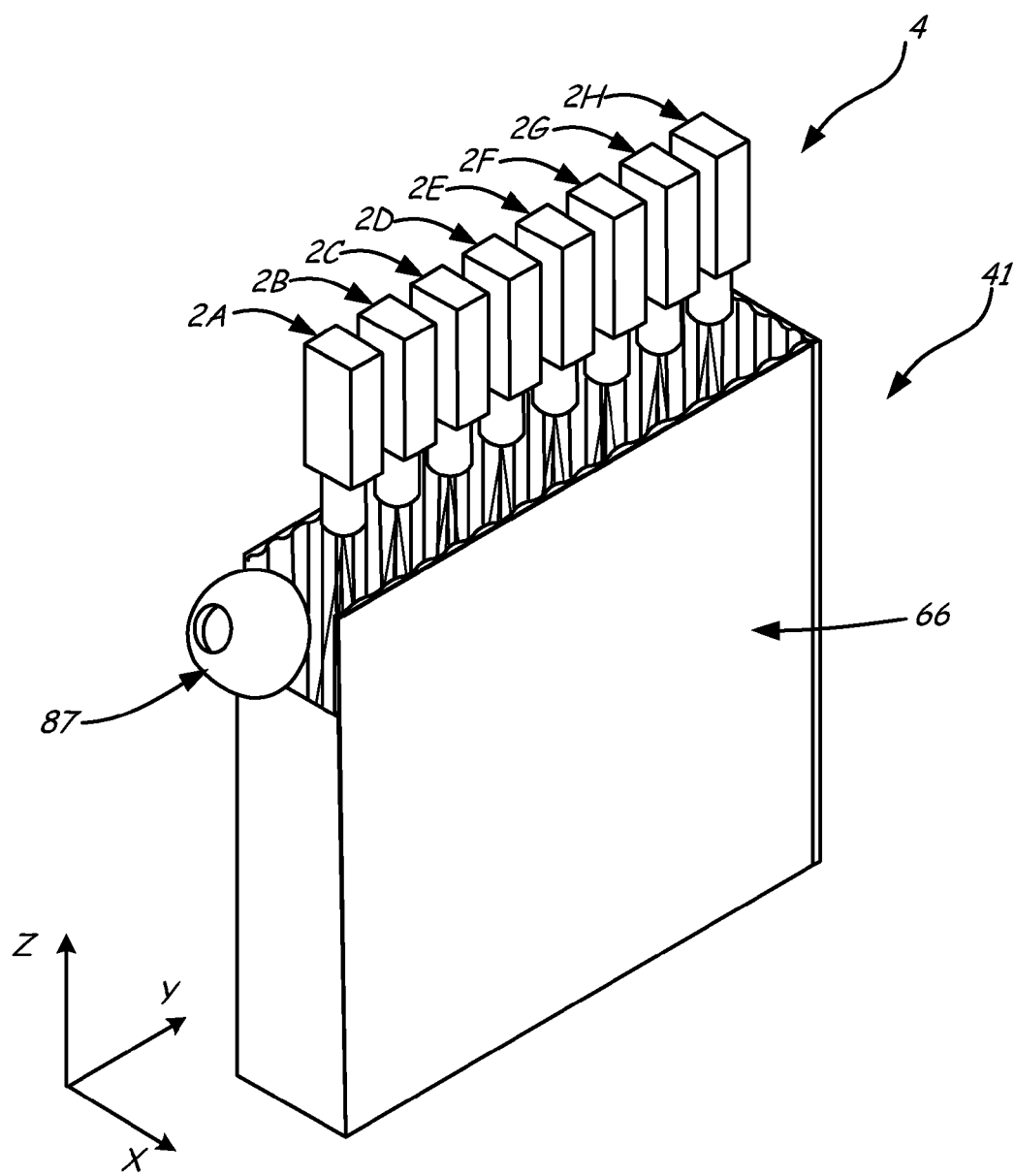
FIG. 15A is a perspective view of a light pipe illuminator and camera array in accordance with an embodiment of the present invention.
Figure 15B:
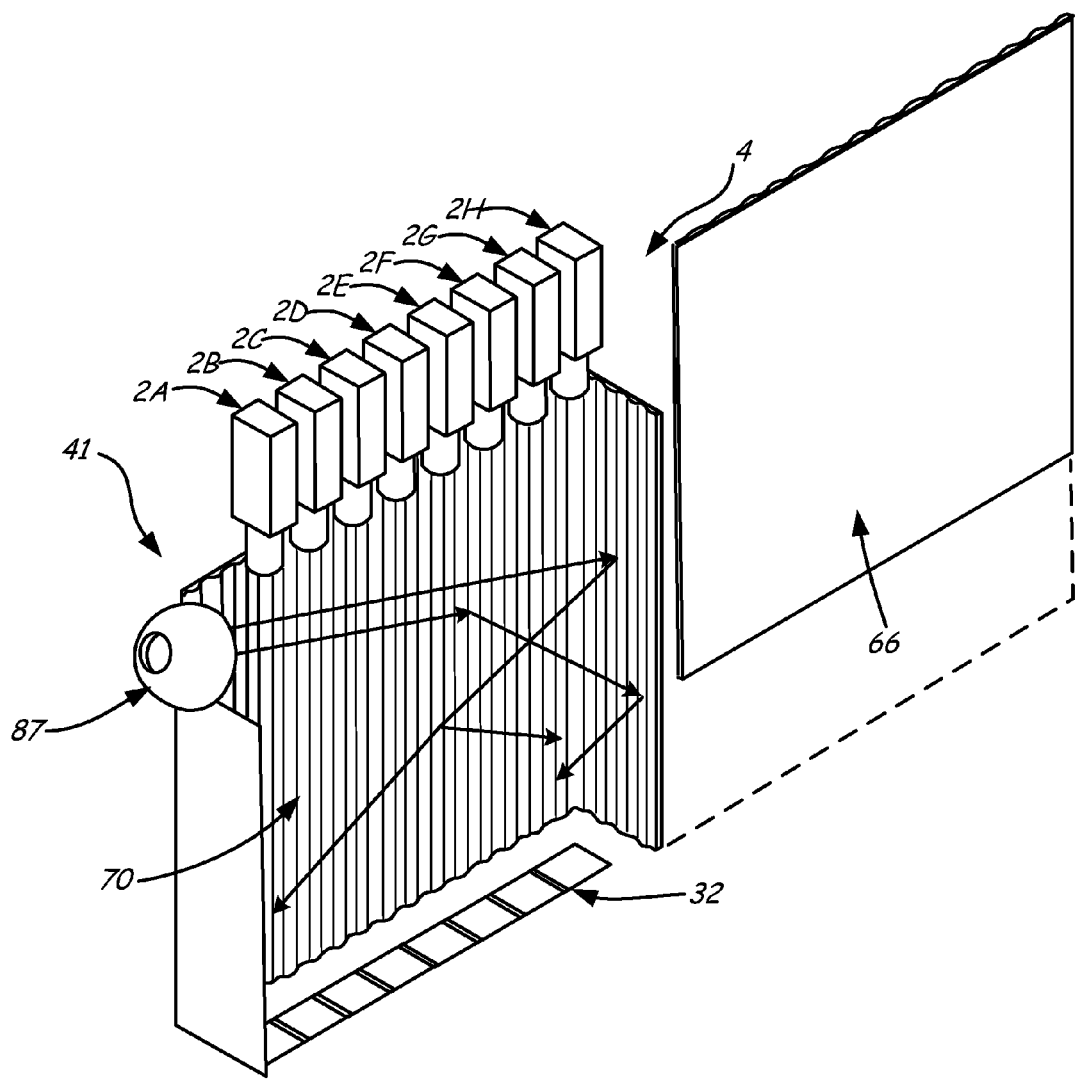
FIG. 15B is a cutaway perspective view of a light pipe illuminator and camera array in accordance with an embodiment of the present invention.
Figure 16:
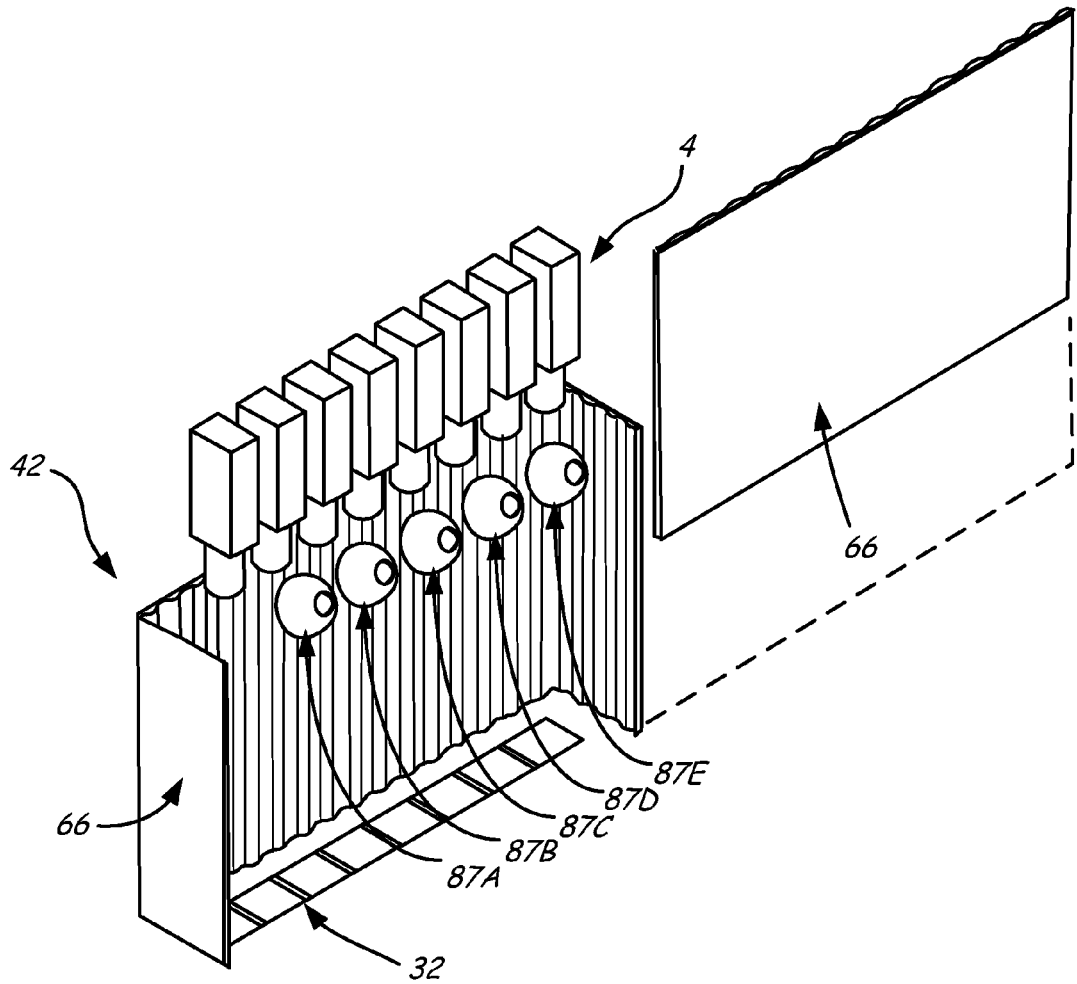
FIG. 16 is a cutaway perspective view of a camera array and illuminator with multiple sources in accordance with an embodiment of the present invention.

FIGS. 15A and 15B show the curved, reflective surfaces applied to the interior surfaces of light pipe illuminator 41 for camera array 4. Light pipe illuminator includes side walls 66 and light source 87. The one-dimensional diffusely reflecting surfaces 70 randomize azimuth angles more rapidly than a light pipe constructed of planar, reflective interior surfaces. This allows a more compact light pipe to be used which allows camera array 4 to be closer to the workpiece. FIG. 15B shows how light rays are randomized in azimuth angle after a small number of reflections.

Light pipe illuminator 42 can be shortened in the Z direction compared to illuminator 41 if multiple light sources are used. Multiple sources, for example a row of collimated LEDs, reduce the total number of reflections required to achieve a spatially uniform source and hence reduce the required light pipe length. Illuminator 42 is illustrated with light sources 87A-87E which may also be strobed arc lamp sources.

Figure 17A:
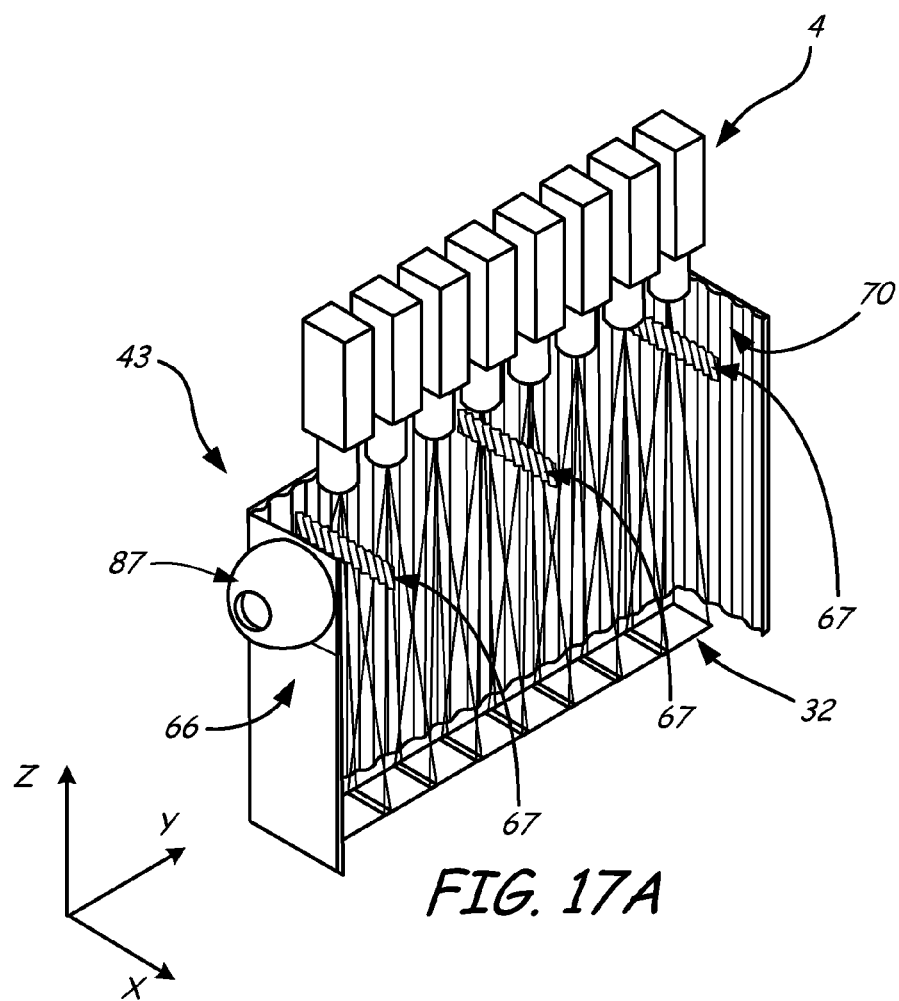
FIG. 17A is a perspective cutaway view of an illuminator and camera array in accordance with an embodiment of the present invention.
Figure 17B:
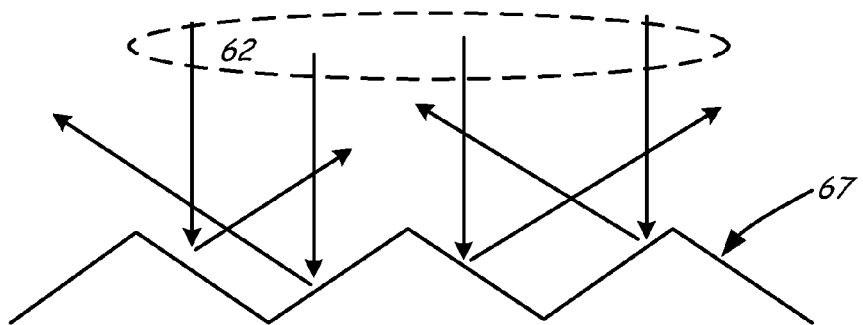
FIG. 17B is a cross sectional view of a chevron shaped mirror employed in accordance with an embodiment of the present invention.

In another aspect of the present invention shown in FIGS. 17A-17B, illuminator 43 includes mirrors 67 that reflect portions of the input beam from source 87 to the desired source elevation angle. Like the multiple source embodiment, this also results in a spatially uniform light field in a shorter light pipe. Mirrors 67 are placed between cameras to avoid blocking the view of the target and at different heights so that each mirror intercepts a portion of the light coming from source 67. Mirrors 67 are shaped to reflect light at the desired elevation angle and toward light pipe side walls 66 where the curved, reflected surfaces 70 rapidly randomize the source azimuth direction. A cross sectional view of mirror 67 is shown in FIG. 17B. Mirror 67 may be, for example, a flat mirror that is formed into a series of chevrons.

Figure 18:
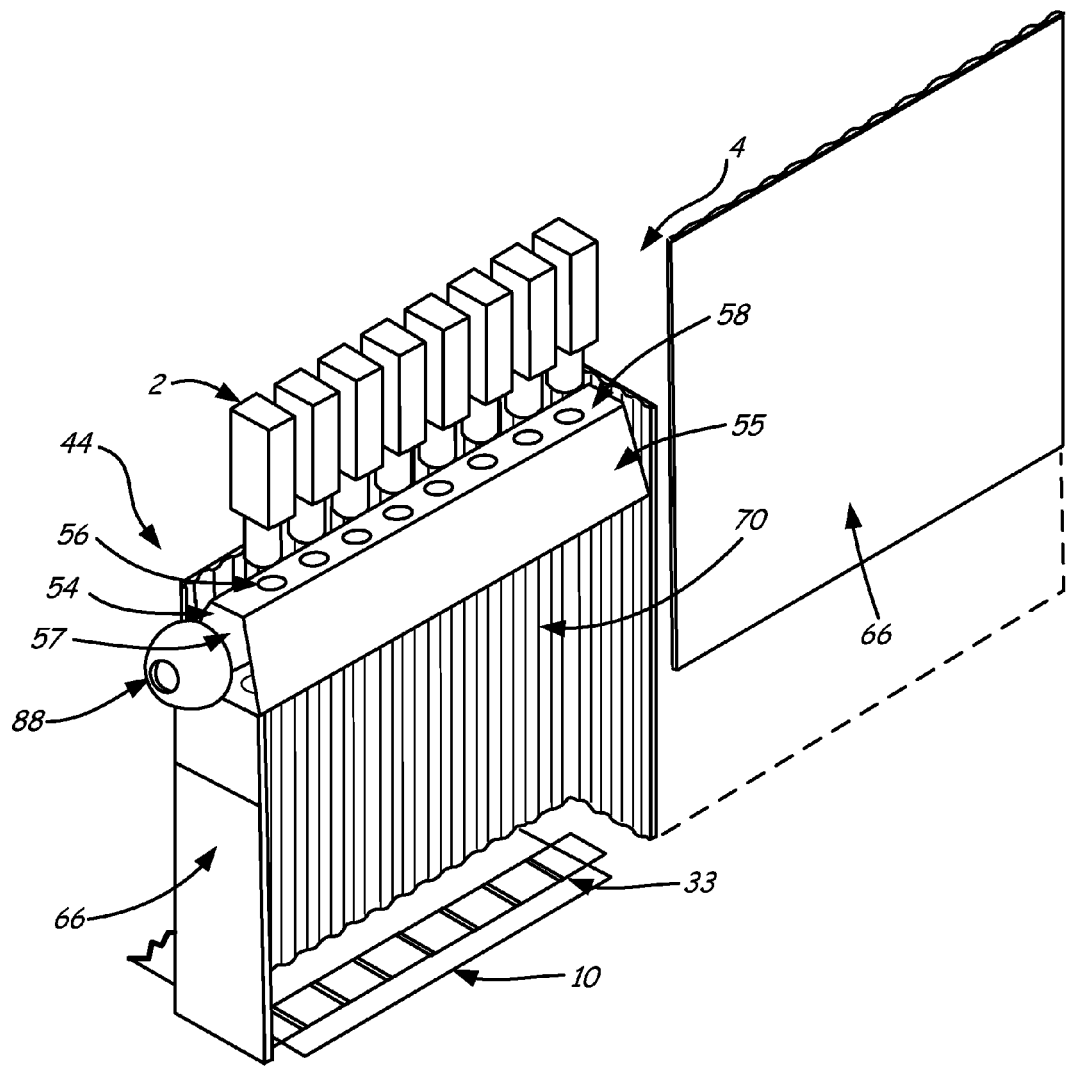
FIG. 18 is a cutaway perspective view of an illuminator and camera array in accordance with an embodiment of the present invention.
Figure 19:
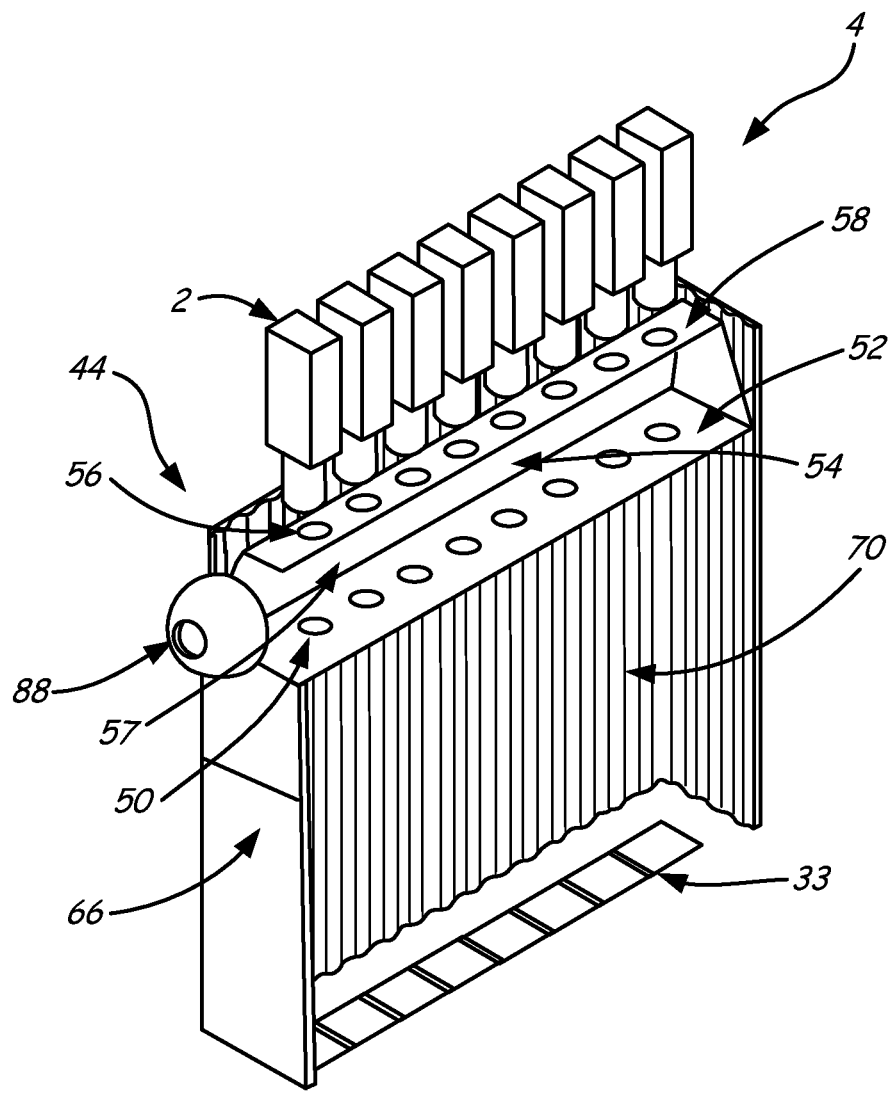
FIG. 19 is a second cutaway perspective view of the illuminator and camera array shown in FIG. 18.

In another embodiment of the present invention, FIGS. 18 and 19 illustrate illuminator 44 integrated with camera array 4. Light is injected by source 88 into light mixing chamber 57 defined by mirrors 54 and 55, top aperture plate 58, and diffuser plate 52. The interior surfaces of 54, 55, and 58 are reflective, whereas diffuser plate 52 is preferably constructed of a translucent, light diffusing material. Apertures 56 are provided on top plate 58 and apertures 50 are provided on diffuser plate 52 such that cameras 2 have an unobstructed view of the workpiece. In order to more clearly visualize diffuser plate 52 and apertures 50, mirror 55 has been removed in FIG. 19, compared with FIG. 18.

Figure 20:
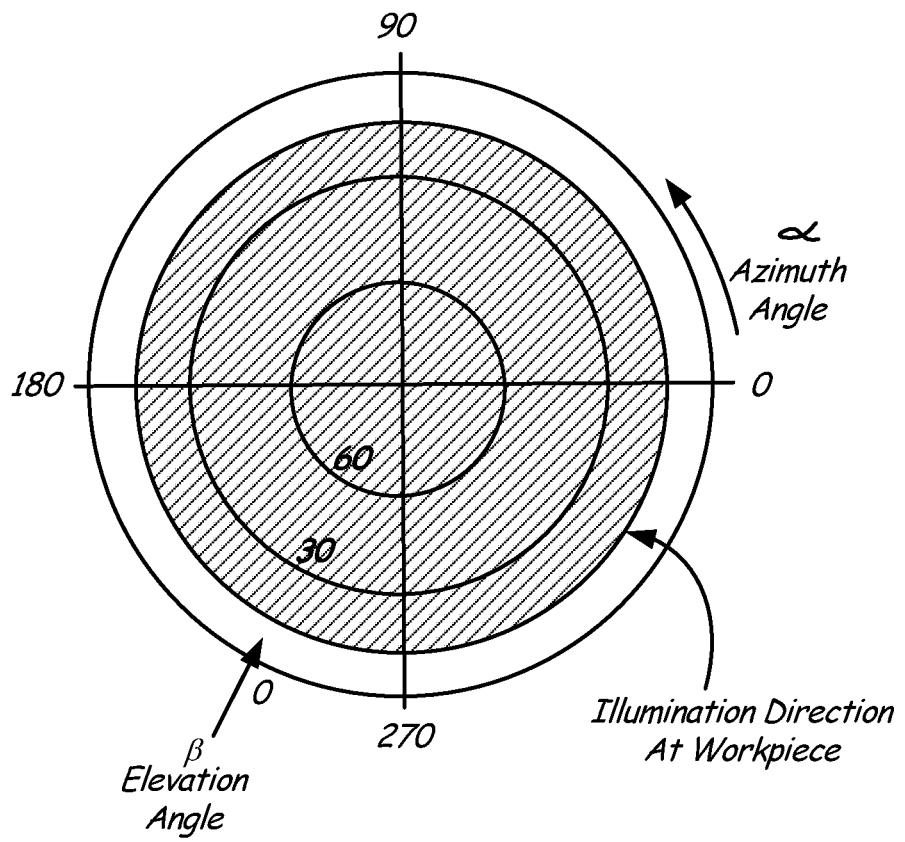
FIG. 20 is a polar plot of the illumination directions of the illuminator shown in FIGS. 18 and 19.

Light projected by source 88 is reflected by mirrors 54 and 55 and aperture plate 58. As the light reflects in mixing chamber 57, diffuser plate 52 also reflects a portion of this light and is injected back into mixing chamber 57. After multiple light reflections within mixing chamber 57, diffuser plate 52 is uniformly illuminated. The light transmitted through diffuser plate 52 is emitted into the lower section of illuminator 44 which is constructed of reflective surfaces 70, such as those discussed with reference to FIGS. 13 and 14. Reflective surfaces 70 preserve the illumination elevation angle emitted by diffuser plate 52. The result is a spatially uniform illumination field at workpiece 10. FIG. 20 is a polar plot showing the output illumination directions of illuminator 44. Illuminator 44 creates an output light field, as shown in FIG. 20, which is termed cloudy day since illumination is nearly equal from almost all elevation and azimuth angles. The range of output elevation angles, however, can be controlled by the diffusing properties of diffuser plate 52.

Figure 21:
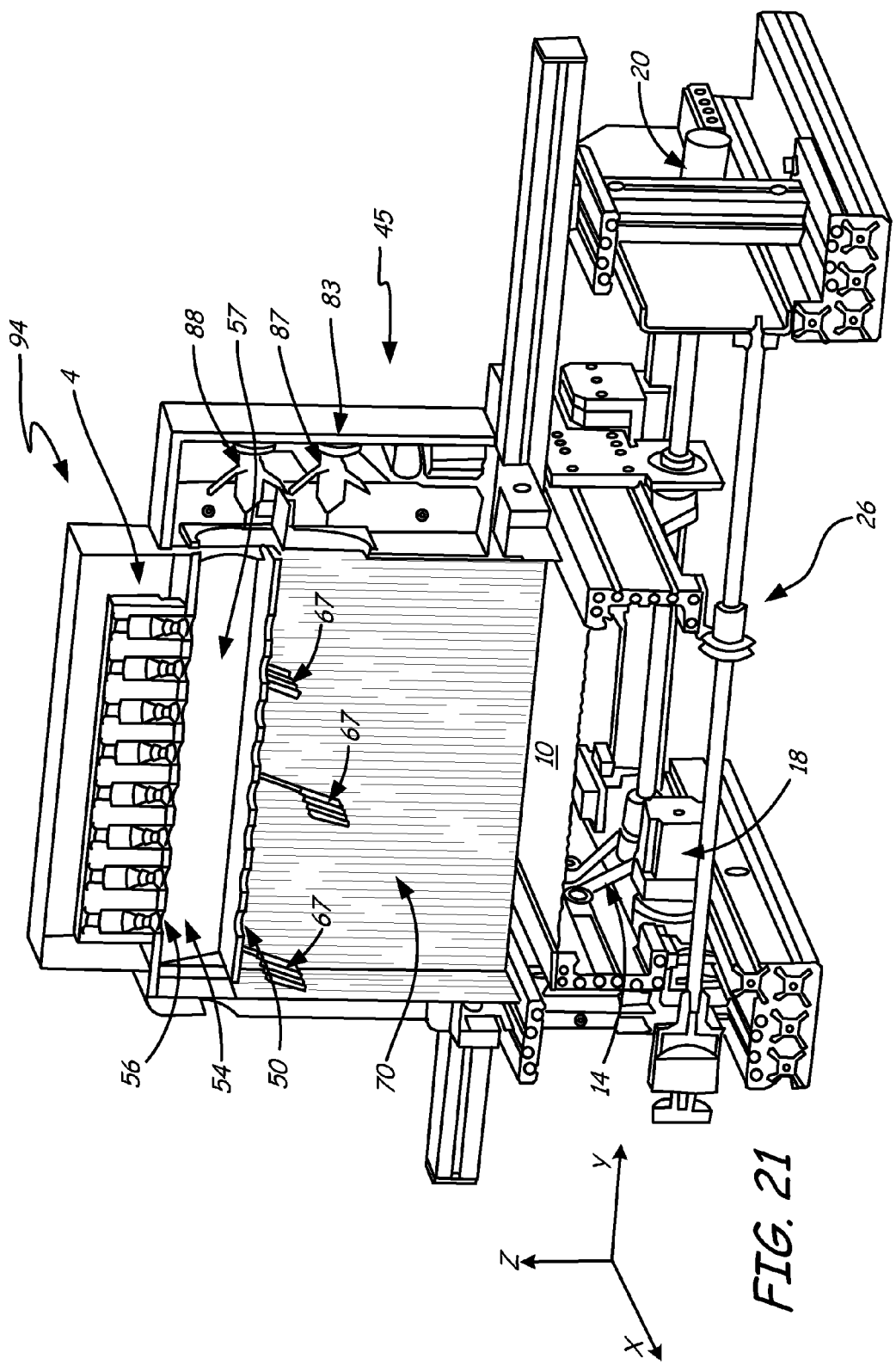
FIG. 21 is a cross-sectional perspective view of an inspection sensor in accordance with an embodiment of the present invention.
Figure 22:
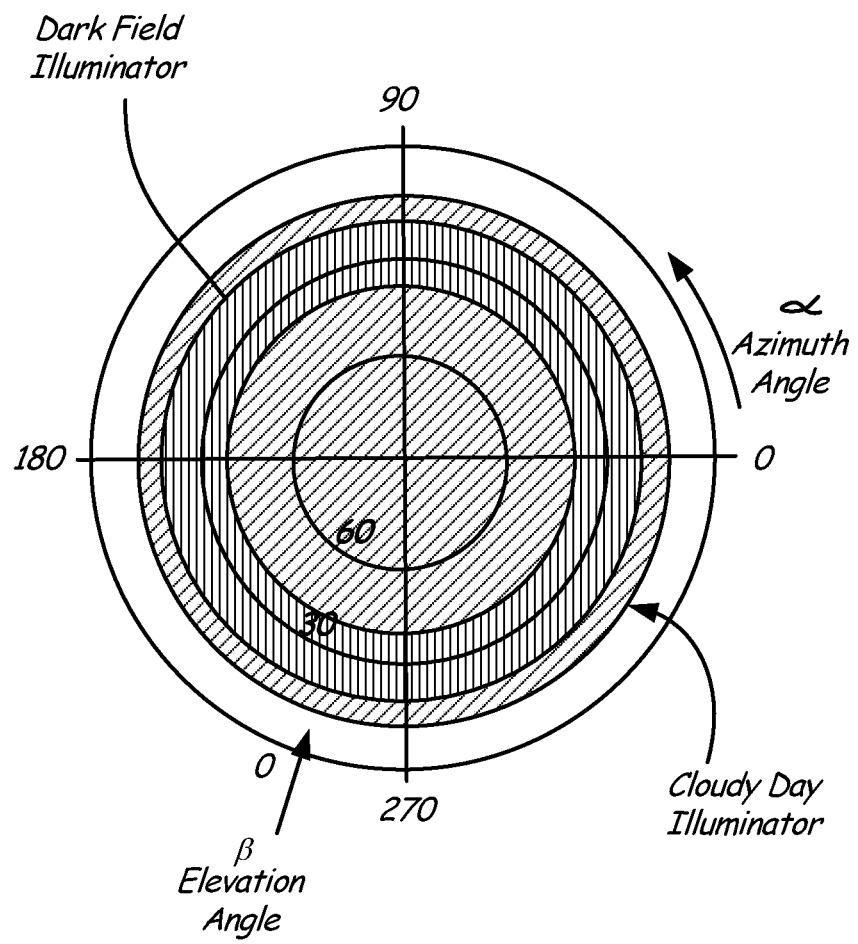
FIG. 22 is a polar plot of the illumination directions of the illuminator shown in FIG. 21.

FIG. 21 shows a preferred embodiment of optical inspection sensor 94. Optical inspection sensor 94 includes camera array 4 and integrated illuminator 45. Illuminator 45 facilitates independently controlled cloudy day and dark field illumination. A dark field illumination field is produced on printed circuit board 10 by energizing light source 87. A cloudy day illumination field is projected onto printed circuit board 10 by energizing light source 88. FIG. 22 shows the polar plot and illumination directions for the cloudy day and dark field illuminations. In one aspect, sources 87 and 88 are strobed to suppress motion blurring effects due to the transport of circuit board 10 in a non-stop manner.

It is understood by those skilled in the art that the image contrast of various object features vary depending on several factors including the feature geometry, color, reflectance properties, and the angular spectrum of illumination incident on each feature. Since each camera array field of view may contain a wide variety of features with different illumination requirements, embodiments of the present invention address this challenge by imaging each feature and location on workpiece 10 two or more times, with each of these images captured under different illumination conditions and then stored into a digital memory. In general, the inspection performance may be improved by using object feature data from two or more images acquired with different illumination field types.

It should be understood that embodiments of the present invention are not limited to two lighting types such as dark field and cloudy day illumination field nor are they limited to the specific illuminator configurations. The light sources may project directly onto workpiece 10. The light sources may also have different wavelengths, or colors, and be located at different angles with respect to workpiece 10. The light sources may be positioned at various azimuthal angles around workpiece 10 to provide illumination from different quadrants. The light sources may be a multitude of high power LEDs that emit light pulses with enough energy to "freeze" the motion of workpiece 10 and suppress motion blurring in the images. Numerous other lighting configurations are within the scope of the invention including light sources that generate bright field illumination fields or transmit through the substrate of workpiece 10 to backlight features to be inspected.

Inspection performance may be further enhanced by the acquisition of three dimensional image data. For example, electrical component polarity marks such as notches, chamfers, and dimples are three dimensional in nature. Acquisition of three dimensional solder paste deposit image data enables measurement of critical height and volume parameters. Further, three dimensional image data can improve segmentation and identification of small features with height relative to the nearly flat substrate.

Three dimensional information such as the profile of a solder paste deposit may be measured using well known laser triangulation, phase profilometry, or moiré methods, for example. U.S. Pat. No. 6,577,405 (Kranz, et al) assigned to the assignee of the present invention describes a representative three dimensional imaging system. Stereo vision based systems are also capable of generating high speed three dimensional image data.

Stereo vision systems are well known. Commercial stereo systems date to the stereoscopes of the 19$^{th}$ century. More recently a great deal of work has been done on the use of computers to evaluate two camera stereo image pairs ("A Taxonomy and Evaluation of Dense Two-Frame Stereo Correspondence Algorithms" by Scharstein and Szeliski) or multiple cameras ("A Space-Sweep Approach to True Multi-Image Matching" by Robert T. Collins). This last reference includes mention of a single camera moved relative to the target for aerial reconnaissance.

To acquire high speed two and three dimensional image data to meet printed circuit board inspection requirements, multiple camera arrays may be arranged in a stereo configuration with overlapping camera array fields of view. The circuit board can then be moved in a nonstop fashion with respect to the camera arrays. Multiple, strobed illumination fields effectively "freeze" the image of the circuit to suppress motion blurring.

Figure 23:
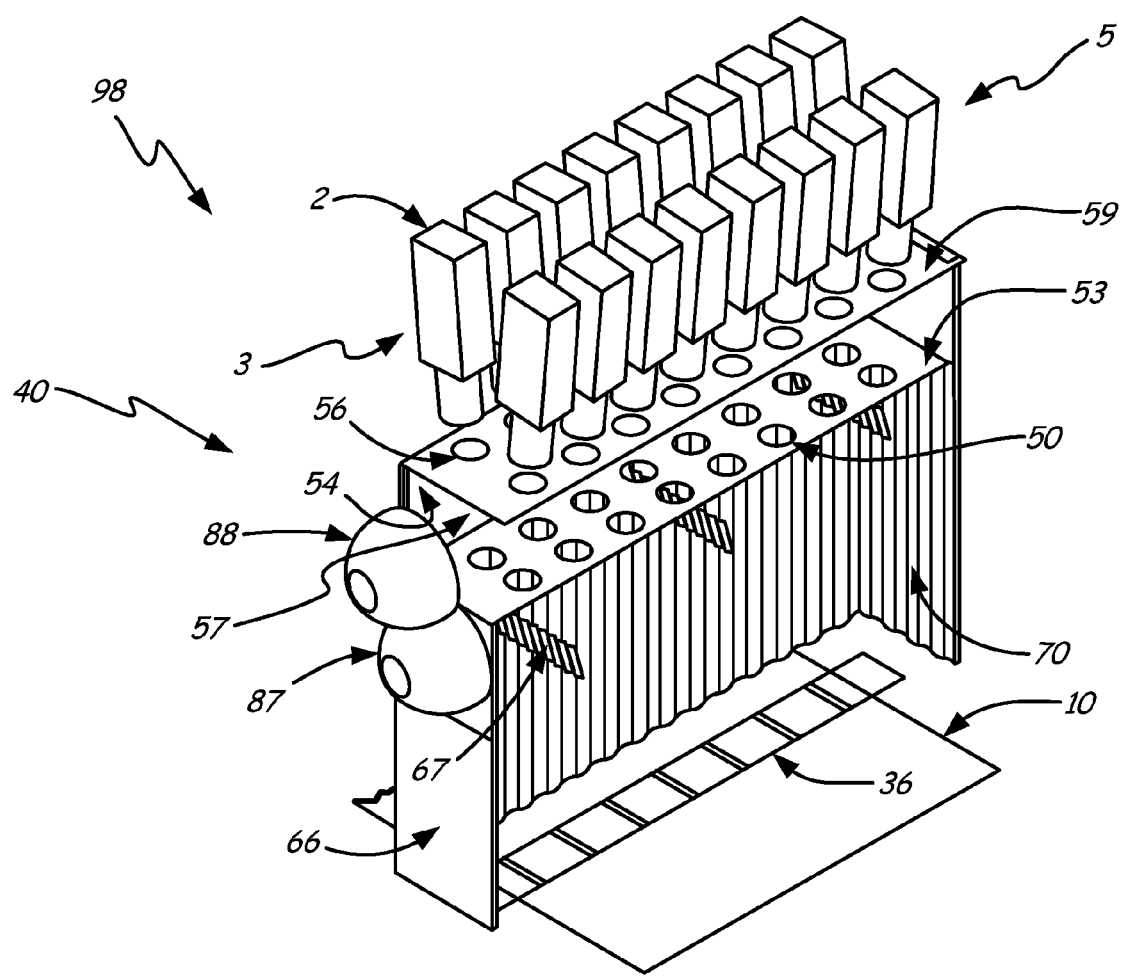
FIG. 23 is a cutaway perspective view of an optical inspection sensor with integrated illuminator for high speed acquisition of stereo image data in accordance with an embodiment of the present invention.

FIG. 23 is a cutaway perspective view of optical inspection sensor 98 with integrated illuminator 40 for high speed acquisition of stereo image data. Camera arrays 3 and 5 are arranged in a stereo configuration with overlapping fields of view 36 on circuit board 10. Circuit board 10 moves in a nonstop fashion relative to inspection sensor 98. Top aperture plate 59 includes apertures 56 and translucent diffuser plate 53 includes apertures 50 to allow unobstructed views of field of view 36 for camera arrays 3 and 5. Energizing light source 88 will create a cloudy day illumination field type on circuit board 10 and energizing light source 87 will create a darkfield illumination field type. Referring back to block diagram FIG. 3, the functional block diagram of optical inspection sensor 98 is very similar to the block diagram of optical inspection sensor 94. For optical inspection sensor 98, however, camera array 4 is removed and replaced by camera arrays 3 and 5 which are in turn interfaced to main electronics board 80. Image memory 82 preferably contains enough capacity to store all images generated by camera arrays 3 and 5 for circuit board 10, or other suitable substrate. Image data is read out of image memory 82 and transferred to system computer 76 over a high speed electrical interface such as PCI Express (PCIe). Application inspection program 71 computes three dimensional image data by known stereo methods using the disparity or offset of image features between the image data from camera arrays 3 and 5.

Figure 24:
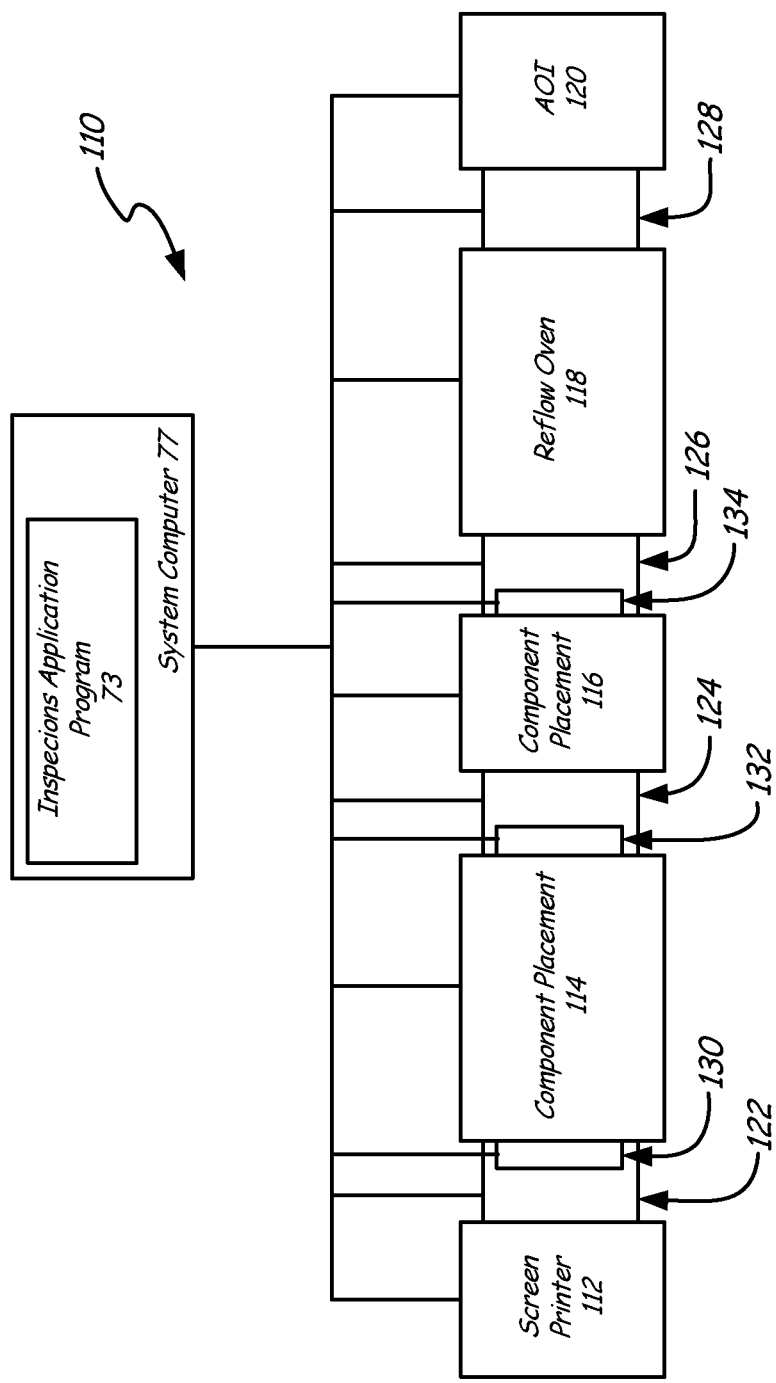
FIG. 24 is a block diagram of an exemplary printed circuit board assembly line that includes an inspection system in accordance with an embodiment of the present invention.
Figure 25:
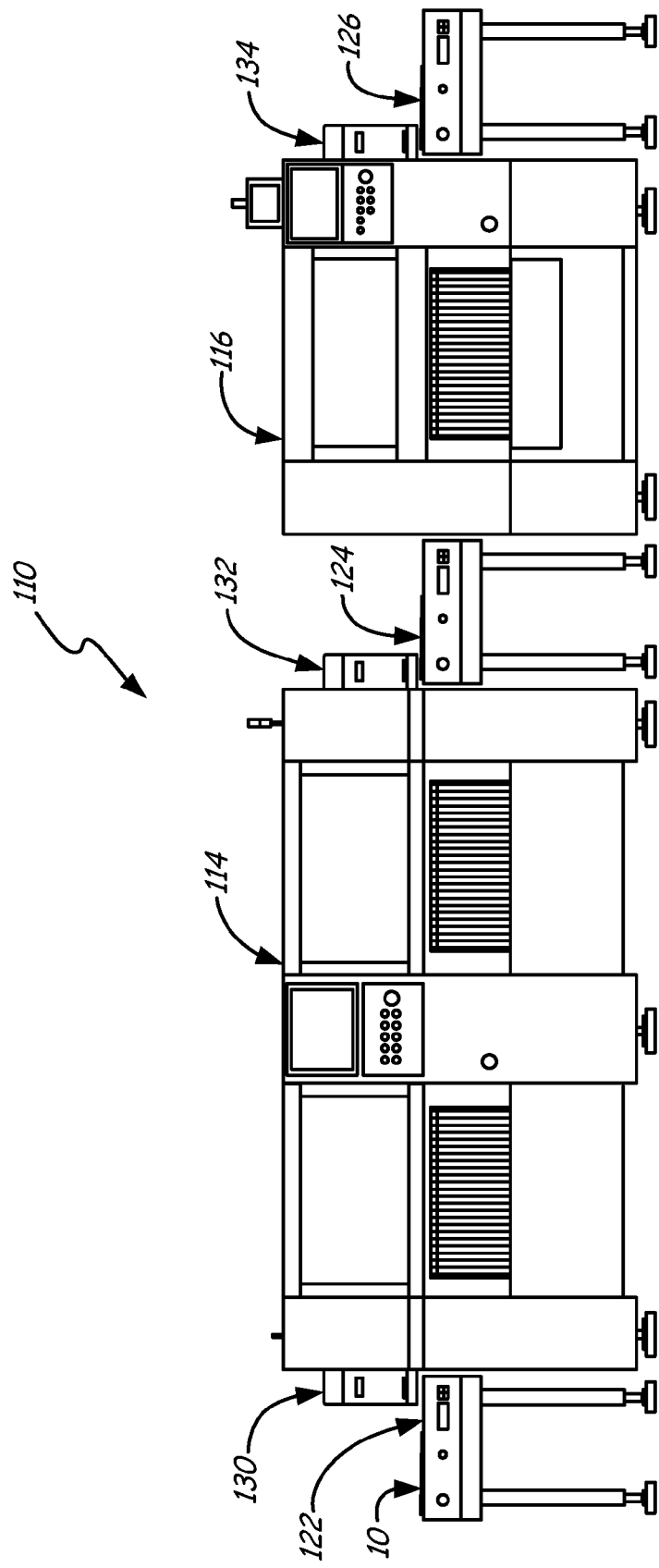
FIG. 25 is a front elevation view of a portion of an assembly line.

FIG. 24 is a block diagram of example automated printed circuit board assembly line 110 that includes an inspection system in accordance with an embodiment of the present invention. Solder paste screen printer 112 prints solder deposits in circuit board 10. A first, high throughput, component placement machine 114 places a number of electrical components on printed circuit board 10. Automated surface mount technology (SMT) assembly lines are often configured with one or more high speed "chip shooter" component placement machines that are optimized to place smaller components such as chip resistors and capacitors at high throughput rates. A second component placement machine 116 is illustrated and is often configured to place a wider range of component styles and sizes, albeit at slower throughput rates. For example, component placement machine 116 may place electrical connectors, ball grid array (BGA) components, flip chip components, quad flat pack (QFP) components, as well as smaller passive electrical components on circuit board 10. Reflow oven 118 melts the solder paste deposits to create mechanical attachment and electrical connection of the components to circuit board 10. Automated optical inspection system 120 provides final inspection of circuit board 10. Conveyors 122, 124, 126, and 128 transport circuit boards between various automated assembly machines in assembly line 110. As used herein a conveyor is intended to mean one or more automatic transport systems that move a workpiece or substrate from one location to another without human assistance. Moreover a conveyor may include an input buffer where workpieces can aggregate prior to an assembly operation. Thus, while a single conveyor 122 is shown coupling screen printer 112 to placement machine 114, such illustration is for clarity since conveyor 122 may include a number of automated system and/or buffers that operate to autonomously carry workpieces from the outlet of screen printer 112 to the inlet of placement machine 114. FIG. 25 is a front elevation view of a portion of assembly line 110.

In a preferred embodiment, optical inspection sensors 130, 132, and 134 are configured similarly to optical inspection sensor 94 shown in FIGS. 1 and 21. In another embodiment, optical inspection sensors 130, 132, and 134 are configured similarly to optical inspection sensor 98 shown in FIG. 23. Computer 77 communicates with the equipment in assembly line 110 and inspection application program 73 computes inspection results using the two dimensional images acquired by optical inspection sensors 130, 132, and 134. Inspection program 73 may also use three dimensional image data to enhance inspection results when optical inspection sensors 130, 132, and 134 are configured to provide stereo or other three dimensional image data. The optional/additional three dimensional image data can be provided for the entire circuit board or selected regions. Inspection sensors 130, 132, and 134 may be situated in close proximity to component placement machines 114 and 116 due to their compact form factors and may be integrated or "embedded" inside the component placement machines. By utilizing multiple optical inspection sensors that are distributed throughout the assembly process, the inspection performance can be improved and the initial programming of the inspection system can be simplified. Inputs to inspection program 73 include fiducial reference indicator locations, and component type, size, location, and polarity which information is known and available from component placement machines 114 and 116. Additional information such component reference designators, the bar code number of circuit board 10, as well as the component feeder number, head number, and nozzle used for a particular component placement are also available from the component placement machines. Solder paste aperture data may be inputted into inspection program 73 from screen printer 112 or an external source.

Inspection application program 73 computes inspection results for solder paste printing such as print registration, area, percent coverage, and unintended bridging between adjacent solder pads. Height and volume may also be computed if three dimensional image data is available. After components are mounted on circuit board 10 by component placement machines 114 and 116, inspection program 73 computes inspection results to verify absence or presence of a component at a particular location on circuit board 10, whether the correct component was placed, the spatial offset of a component from its nominal design location, the spatial offset with respect to the solder paste print, and whether a component was mounted with the correct polarity. Inspection program 73 also computes whether a stray component was inadvertently released onto circuit board 10 at an improper location such as where another component is to be mounted during a subsequent placement operation.

During the assembly process and after solder paste screen printing, conveyor 122 transports printed circuit board 10 into component placement machine 114 in a non-stop fashion while inspection sensor 130 acquires images of circuit board 10 with one or more illumination field types. These images are transmitted to computer 77 and are made available to inspection application program 73 where the solder paste deposits are identified and the solder paste inspection results are generated.

Component placement machine 114 then places a portion of electrical components onto circuit board 10. When the assembly operation by component placement machine 114 is complete, conveyor 124 facilitates transport of circuit board 10 in a non-stop fashion while optical inspection sensor 132 acquires images of circuit board 10 with one or more illumination types. These images are transmitted to computer 77 and are made available to inspection program 73. Inspection program 73 computes inspection results for component presence/absence, correct component, spatial offset, and component polarity for components placed by placement machine 114. The component offset with respect to the solder paste deposits is also computed by inspection program 73 by using images captured before and after the component placement operation as explained with respect to FIGS. 26A-26C.

Figure 26A:
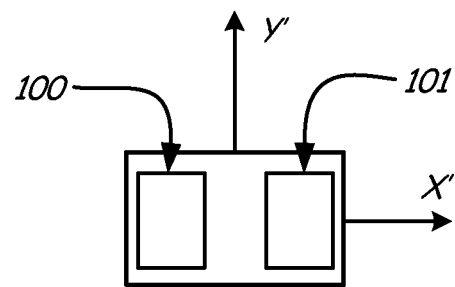
FIG. 26A is a diagrammatic view of exemplary solder paste deposits identified by an inspection program in accordance with an embodiment of the present invention.
Figure 26B:
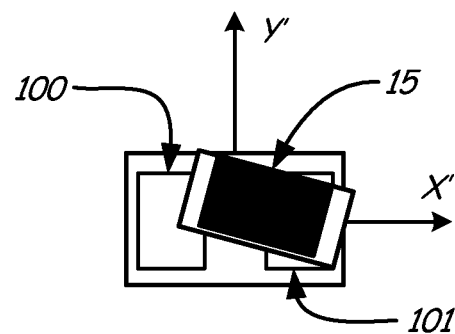
FIG. 26B is a diagrammatic view of an exemplary image of the same region depicted in FIG. 26A captured with an optical inspection sensor after an assembly operation in accordance with an embodiment of the present invention.
Figure 26C:
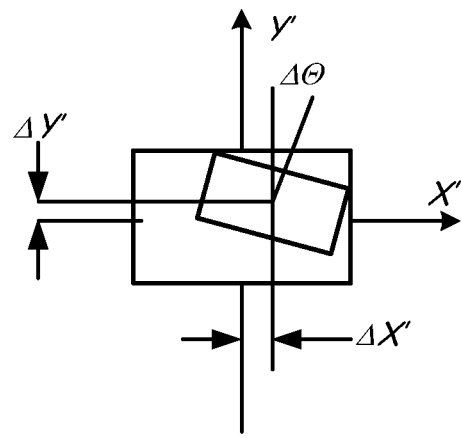
FIG. 26C is a diagrammatic view of a difference image between FIGS. 26A and 26B.

FIG. 26A shows example solder paste deposits 100 and 101 on circuit board 10 identified by inspection program 73 using the images acquired with optical inspection sensor 130 before the assembly operation of component placement machine 114. Local coordinate axes X', Y' are shown that define the location of the solder paste deposits. FIG. 26B shows an example image of the same region of circuit board 10 that has been captured by optical inspection sensor 132 after the assembly operation of component placement machine 114. Component 15 was placed on circuit board 10 by component placement machine 114. Inspection program 73 registers the images captured before and after the component placement operation and then performs a difference operation on the registered images. Spatial offsets $\Delta X'$, $\Delta Y'$, and $\Delta \theta'$ for component 15 are computed by inspection program 73 using this difference image and the results are shown in FIG. 26C.

With the industry trend of electrical component sizes shrinking ever smaller, there is a risk of component placement machine 114 inadvertently releasing a component at an improper location on circuit board 10. For example, if this so-called stray component was released onto the location where a subsequent ball grid array (BGA) component was to be mounted by component placement machine 114, then this error would go undetected by AOI machine 120 since the stray component would not be visible. Circuit board 10 would not function as intended which may result in it being scrapped, or at least, the faulty BGA site would have to be diagnosed by other methods and reworked at significant cost. Inspection program 73 identifies stray components as explained with respect to FIGS. 27A-27C.

Figure 27A:
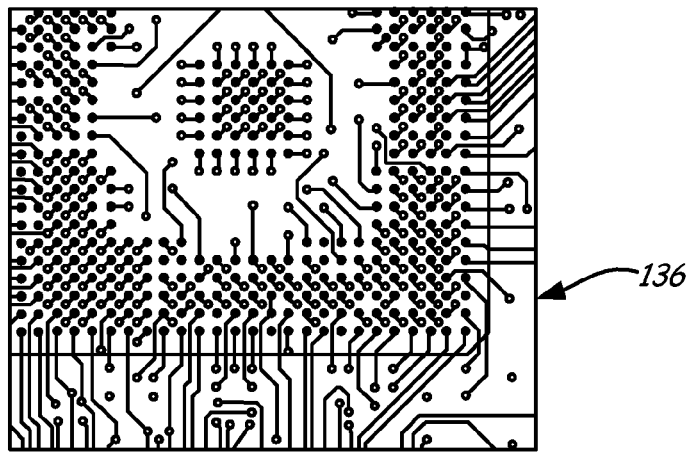
FIG. 27A is a diagrammatic view of an exemplary image acquired by an optical inspection system in accordance with an embodiment of the present invention.
Figure 27B:
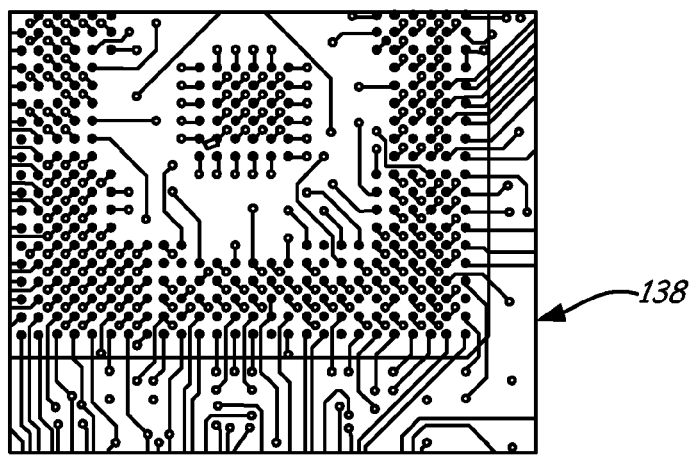
FIG. 27B is a diagrammatic view of an exemplary image acquired by an optical inspection sensor where a stray component has been placed.
Figure 27C:
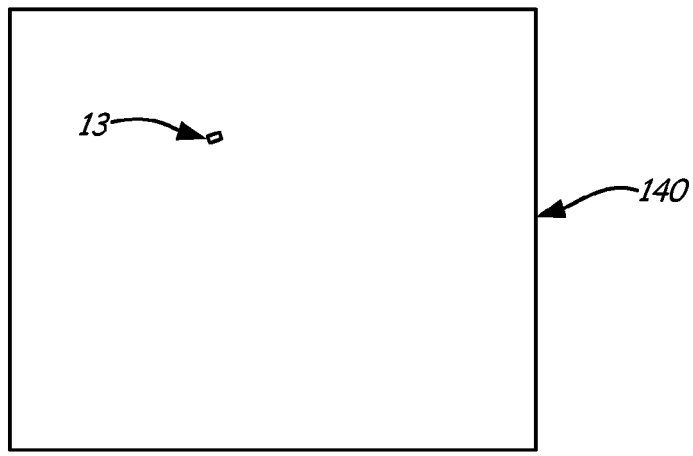
FIG. 27C is a diagrammatic difference image between FIGS. 27A and 27B.

FIG. 27A shows example image 136 acquired by optical inspection sensor 130 in the region of where a BGA will be placed by component placement machine 116. FIG. 27B shows example image 138 acquired by optical inspection sensor 132 in the same region and where a stray component has been inadvertently released onto circuit board 10 by component placement machine 114. Inspection program 73 registers images 136 and 138 and computes the difference image 140 shown in FIG. 27C. Since no components are intended to be placed in this region by placement machine 114, the presence of component 13 in image 140 is an indication of a stray component. The assembly process may then be halted before additional components are added to circuit board 10 and additional expense incurred. Acquiring images 136 and 138 before and after an assembly step simplifies the initial programming of inspection program 73 since the difference image segments the stray component from numerous other valid features.

When the assembly operation by component placement machine 116 is complete, conveyor 126 facilitates transport of circuit board 10 in a non-stop fashion while optical inspection sensor 134 acquires images of circuit board 10 with one or more illumination types. These images are transmitted to computer 77 and are made available to inspection program 73. Inspection program 73 then computes inspection results for presence/absence, correct component, spatial offset, polarity, and offset with respect to the solder paste deposits for the remaining portion of components placed onto circuit board 10 by placement machine 116.

AOI machine 120 computes results such as verifying component presence/absence, location, polarity, and proper solder joint fillets after the solder has been reflowed by oven 118. However, AOI machine 120 cannot identify stray components at BGA or other larger component sites since they are no longer visible. When AOI machine 120 does detect an error, it is often difficult to determine the root cause of an assembly error at that stage in the assembly process. To facilitate improved root cause failure analysis, inspection program 73 can provide images of circuit board 10 to the defect review subsystem of AOI machine 120 that were captured by optical inspection sensors 130, 132, and 134 at the various stages of the assembly process and in the region of the defect identified by AOI machine 120. These images help narrow the list of potential assembly error sources and speed up root cause failure analysis.

Although the present invention has been described with reference to preferred embodiments, workers skilled in the art will recognize that changes may be made in form and detail without departing from the spirit and scope of the invention.

What is claimed is:

1. An electronics assembly line comprising:
   a first electronics assembly machine, having a first electronics assembly machine outlet;
   a second electronics assembly machine having a second electronics assembly machine inlet and outlet, the inlet of the second electronics assembly machine being coupled to the outlet of the first electronics assembly machine by a conveyor;
   a first optical inspection sensor disposed over the conveyor before the inlet of the second electronics assembly and configured to provide first sensor inspection image data relative to a substrate that passes beneath the first optical inspection sensor in a non-stop fashion;
   a second optical inspection sensor disposed over a conveyor after the outlet of the second electronics assembly machine and configured to provide second sensor inspection image data relative to a substrate that passes beneath the second optical inspection sensor in a non-stop fashion; and
   a computer operably coupled to the first and second optical inspection sensors, the computer being configured to provide an inspection result based upon at least one of the first and second inspection image data.

2. The electronics assembly line of claim 1, wherein the second electronics assembly machine is a component placement machine.

3. The electronics assembly line of claim 2, wherein the first electronics assembly machine is a solder paste screen printer.

4. The electronics assembly line of claim 2, wherein the first electronics assembly machine is a component placement machine.

5. The electronics assembly line of claim 1, wherein at least one of the first and second optical inspection sensors includes at least one array of cameras disposed in a line perpendicular to a direction of conveyor movement.

6. The electronics assembly line of claim 5, wherein the at least one of the first and second optical inspection sensors includes an illuminator configured to provide a plurality of illumination field types through a light pipe, and wherein the at least one array of cameras is disposed to view the substrate through the light pipe.

7. The electronics assembly line of claim 6, wherein the at least one array includes a plurality of arrays configured to provide stereoscopic imaging such that at least one of the first and second inspection image data is three-dimensional image data.

8. The electronics assembly line of claim 7, wherein the three-dimensional image data is provided for substantially an entire substrate.

9. The electronics assembly line of claim 7, wherein the three-dimensional image data is provided for at least one selected region of the substrate.

10. The electronics assembly line of claim 1, wherein the inspection result is based upon the first and second inspection image data.

11. The electronics assembly line of claim 1, wherein the inspection result is indicative of a stray component.

12. The electronics assembly line of claim 11, wherein a difference image is used to determine the inspection result.

13. The electronics assembly line of claim 1, wherein the inspection result is indicative of offset measurement with respect to solder paste print.

14. The electronics assembly line of claim 1, wherein the inspection result is indicative of component presence.

15. The electronics assembly line of claim 1, wherein the inspection result is indicative of a correct component.

16. The electronics assembly line of claim 1, wherein the inspection result is indicative of a spatial offset of a component from a nominal design location.

17. The electronics assembly line of claim 1, wherein the inspection result is indicative of solder paste inspection information.

18. The electronics assembly line of claim 17, wherein the inspection result is indicative of solder paste registration.

19. The electronics assembly line of claim 1, wherein the inspection result is indicative of at least one parameter selected from the group consisting of solder paste area, solder paste percent coverage, solder paste bridging, solder paste height, and solder paste volume.

20. The electronics assembly line of claim 1, wherein the computer executes an inspection program that receives the first and second optical inspection image data and takes as an additional input at least one parameter selected from the group consisting of fiducial reference indicator locations, component type, component size, component location, component reference designator, polarity, and solder paste aperture data.

21. The electronics assembly line of claim 1, wherein at least one of the first and second inspection image data is provided to an external device.

22. The electronics assembly line of claim 21, wherein the external device is an automated optical inspection (AOI) machine.

23. The electronics assembly line of claim 21, wherein at least one of the first and second inspection image data is used to facilitate root cause analysis.

24. An electronics assembly machine having an inlet and an outlet, the machine comprising:
a first optical inspection sensor disposed relative to the inlet to image a substrate prior to an assembly operation, while the substrate undergoes relative motion with respect to the first optical inspection sensor, the first optical inspection sensor being configured to provide first sensor inspection image data relative to the substrate;
a second optical inspection sensor disposed to image the substrate after an assembly operation by the electronics assembly machine, while the substrate undergoes relative motion with respect to the second optical inspection sensor, the second optical inspection sensor being configured to provide second sensor inspection image data relative to the substrate;
a computer operably coupled to the first and second optical inspection sensors, the computer being configured to provide an inspection result based upon at least one of the first and second inspection image data.

* * * * *

UNITED STATES PATENT AND TRADEMARK OFFICE
CERTIFICATE OF CORRECTION

| | | |
|---|---|---|
| PATENT NO. | : 8,872,912 B2 | Page 1 of 1 |
| APPLICATION NO. | : 12/940214 | |
| DATED | : October 28, 2014 | |
| INVENTOR(S) | : Steven K. Case et al. | |

It is certified that error appears in the above-identified patent and that said Letters Patent is hereby corrected as shown below:

In the Claims

Column 18

Line 31: insert a space between "leastone" so that it reads "least one"

Line 32: insert a space between "inspectionimage" so that it reads "Inspection image"

Signed and Sealed this
Eighth Day of March, 2016

Michelle K. Lee
*Director of the United States Patent and Trademark Office*